US011033600B2

(12) United States Patent
Chang et al.

(10) Patent No.: US 11,033,600 B2
(45) Date of Patent: Jun. 15, 2021

(54) PROTEASE TRANSITION STATE INHIBITOR PRODRUGS

(71) Applicants: Kansas State University Research Foundation, Manhattan, KS (US); Wichita State University, Wichita, KS (US)

(72) Inventors: Kyeong-Ok Chang, Manhattan, KS (US); William C. Groutas, Wichita, KS (US)

(73) Assignees: Kansas State University Research Foundation, Manhattan, KS (US); Wichita State University, Wichita, KS (US)

( * ) Notice: Subject to any disclaimer, the term of this patent is extended or adjusted under 35 U.S.C. 154(b) by 12 days.

(21) Appl. No.: 16/320,681

(22) PCT Filed: Jul. 28, 2017

(86) PCT No.: PCT/US2017/044485
§ 371 (c)(1),
(2) Date: Jan. 25, 2019

(87) PCT Pub. No.: WO2018/023054
PCT Pub. Date: Feb. 1, 2018

(65) Prior Publication Data
US 2019/0151400 A1    May 23, 2019

Related U.S. Application Data

(60) Provisional application No. 62/367,702, filed on Jul. 28, 2016.

(51) Int. Cl.
| | |
|---|---|
| *A61K 38/00* | (2006.01) |
| *A61K 38/05* | (2006.01) |
| *A61K 31/4015* | (2006.01) |
| *A61K 31/662* | (2006.01) |
| *A61K 31/223* | (2006.01) |
| *C07K 5/06* | (2006.01) |
| *A61K 31/225* | (2006.01) |
| *A61K 31/5375* | (2006.01) |
| *A61K 47/50* | (2017.01) |
| *A61P 31/14* | (2006.01) |
| *A61K 47/10* | (2017.01) |
| *A61K 45/06* | (2006.01) |

(52) U.S. Cl.
CPC ............ *A61K 38/05* (2013.01); *A61K 31/223* (2013.01); *A61K 31/225* (2013.01); *A61K 31/4015* (2013.01); *A61K 31/5375* (2013.01); *A61K 31/662* (2013.01); *A61K 47/10* (2013.01); *A61K 47/50* (2017.08); *A61P 31/14* (2018.01); *C07K 5/06* (2013.01); *A61K 45/06* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 4,756,845 | A | * | 7/1988 | Sugawara .............. C11D 3/392 252/186.38 |
| 5,132,400 | A | | 7/1992 | Gammill et al. |
| 2015/0133368 | A1 | | 5/2015 | Chang et al. |

FOREIGN PATENT DOCUMENTS

| | | |
|---|---|---|
| WO | 1996015132 | 5/1996 |
| WO | 2003078438 | 9/2003 |
| WO | 2013049382 | 4/2013 |

OTHER PUBLICATIONS

Your Dictionary, Alkoxy, available online at: https://www.yourdictionary.com/alkoxy, accessed on Sep. 28, 2020. (Year: 2020).*
International Search Report and Written Opinion in corresponding PCT/US2017/044485, dated Jan. 2, 2018.
Mandadapu, et al., "Inhibition of norovirus 3CL protease by bisulfite adducts of transition state inhibitors", Bioorg Med Chem Lett. Jan. 1, 2013; 23(1):62-5.

* cited by examiner

*Primary Examiner* — Jeanette M Lieb
(74) *Attorney, Agent, or Firm* — Hovey Williams LLP

(57) ABSTRACT

Disclosed herein are protease transition state inhibitor/analogue prodrug compounds selected from the group consisting of esters, carbamates, ester phosphates, and pharmaceutically acceptable salts thereof. Compositions containing such prodrugs are also disclosed, along with methods of using such compounds therapeutically or prophylactically against calicivirus, picornavirus, and/or coronavirus infection, as well as other conditions, such as malaria, cancer, stroke, heart attack, neural degeneration, cataracts, and glaucoma through inhibition of the variety of proteases associated with progression of such conditions.

Figure 1A:
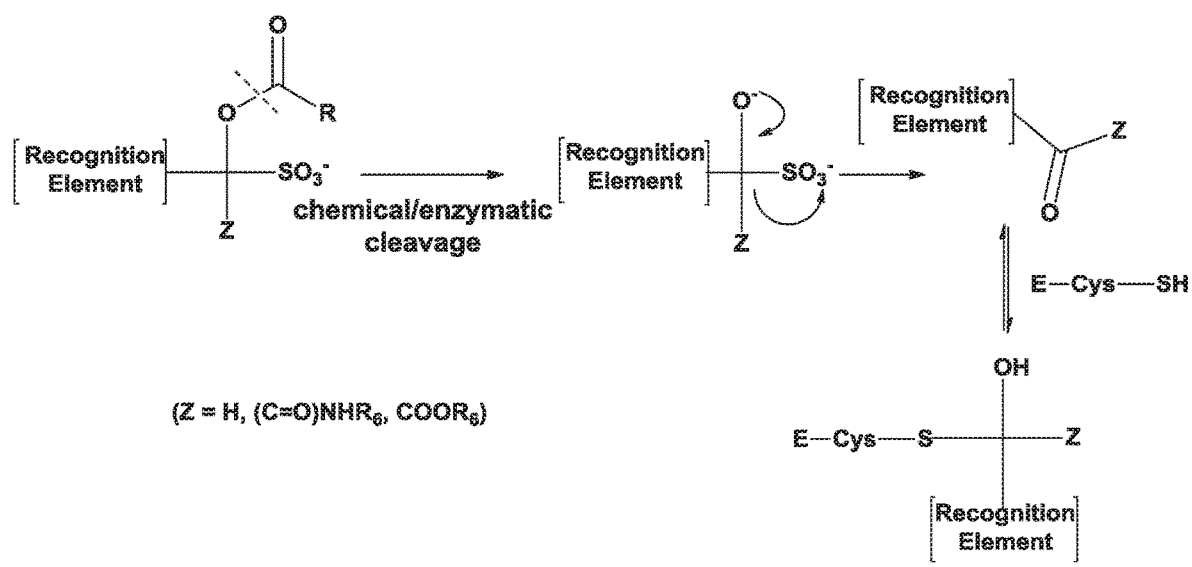

19 Claims, 5 Drawing Sheets
Specification includes a Sequence Listing.

a. EDCI/HOBt/DIEA/DMF then Gln surrogate; b. 2M LiBH₄/THF/CH₃OH; c. Dess-Martin periodinane/DCM; d. C₂H₅OH/EtOAc/NaHSO₃; e. Alkanoic anhydride/CH₃CN/Reflux 2h; f. Amino acid isocyanate/CH₃CN/ Reflux 2h.

PROTEASE TRANSITION STATE INHIBITOR PRODRUGS

CROSS-REFERENCE TO RELATED APPLICATIONS

The present application is the U.S. National Stage of International Patent Application No. PCT/US2017/044485, filed Jul. 28, 2017, which claims the priority benefit of U.S. Provisional Patent Application Ser. No. 62/367,702, filed Jul. 28, 2016, entitled Prodrugs of Bisulfite Adducts of Transition State Inhibitors of Serine and Cysteine Proteases: A General Strategy for Optimizing Physicochemical Properties and Pharmacokinetics, each of which is incorporated by reference in its entirety herein.

FEDERALLY SPONSORED RESEARCH OR DEVELOPMENT

This invention was made with government support under R01AI109039 awarded by the National Institutes of Health. The government has certain rights in the invention.

SEQUENCE LISTING

The nucleic and amino acid sequences listed in the accompanying Sequence Listing are presented in accordance with 37 C.F.R. 1.822. The Sequence Listing is submitted as an ASCII computer readable text file, created on Jul. 26, 2017, 1 KB, which is incorporated by reference herein.

BACKGROUND OF THE INVENTION

Field of the Invention

The present invention relates to prodrugs of serine and cysteine protease transition state inhibitor compounds.

Description of Related Art

Proteases are pivotal regulators of physiologic processes with abundant mechanisms for the balance of their activation and inhibition. The disturbance of the balance (overactivation) usually leads to abnormal development, poor health, disease, and even death. Consequently, proteases are therapeutic targets for many diseases including hypertension, cancer, inflammation, etc. Furthermore, many pathogenic microbes carry proteases and protease function is crucial for successful infection, which makes them ideal therapeutic targets. For example, human noroviruses are the principal cause of non-bacterial acute gastroenteritis worldwide, and morbidity is particularly high among the young and elderly, as well as immunocompromised individuals. The problem is further exacerbated by the high infectivity, genetic diversity, copious virus shedding, and environmental stability of noroviruses. Other factors that compound the problem and hamper drug discovery efforts include the lack of a robust animal model that recapitulates all aspects of the disease, the fact that human noroviruses are extremely difficult to culture, and an incomplete understanding of norovirus biology and pathogenesis. Collectively, the management of norovirus infections presents a challenge because no effective vaccines or norovirus-specific therapeutics or prophylactics are currently available. Among positive sense RNA viruses, certain viruses can be classified as members of the picornavirus-like "supercluster," which includes picornaviruses, caliciviruses, and coronaviruses. A common feature of these viruses is that they possess a viral 3C or 3C-like (3CL) protease which is responsible for most cleavages of the corresponding viral polyprotein. These 3C and 3CL proteases share some common characteristics, including a typical chymotrypsin-like fold and a catalytic triad (or dyad) with Cys-His-Glu (or Asp) on the protease, and a preference for a Glu or Gln residue at the P1 position on the substrate.

As part of an ongoing research program focused on the discovery of antiviral therapeutics and prophylactics for norovirus and picornaviral infections, structure-guided design, synthesis and in vitro biochemical evaluation of peptidyl aldehydes, α-ketoamide, and α-ketoheterocycle transition state (TS) inhibitors of norovirus 3CL protease and related picornaviral 3C and 3CL proteases, has been reported. These inhibitors were found to potently inhibit norovirus in a cell-based replicon system and to exhibit efficacy in a small animal model of norovirus infection. However, the therapeutic potential of these inhibitors, particularly aldehyde-based inhibitors, is adversely impacted by their sub-optimal pharmacokinetics (rapid metabolism) and low oral bioavailability. While there have been other successes in protease inhibitor drug development including antiviral (HIV, HCV), anti-cancer and others, most protease inhibitor drug development has failed due to sub-optimal pharmacokinetics (PK) and/or oral bioavailability of the inhibitors. These features preclude their development as therapeutics. Therefore, improvement of PK and oral bioavailability of protease inhibitors is crucial for their successful drug development.

As a first step toward circumventing this limitation, prior work introduced the use of aldehyde bisulfite adduct salts as a latent (masked) form of the aldehyde functionality. However, improvements to PK and bioavailability are still needed.

SUMMARY OF THE INVENTION

The present invention is broadly concerned with prodrug forms (ester, carbamate) of aldehyde bisulfite adducts and phosphates, and general approaches for generating ester or carbamate prodrug forms of various transition state inhibitor compounds to improve their PK and bioavailability. In one aspect, protease transition state inhibitor prodrug compounds are described that can be used as therapeutic or prophylactic compounds against a variety of conditions, including viral infection. malaria, cancer (tumor cell growth), stroke, heart attack, neural degeneration, cataracts, and glaucoma. The prodrugs act as transition state inhibitors or mimics to disrupt protease activity, and accordingly initiation or progression of the condition (which relies on functional protease activity).

Metabolism can be modulated by varying the hydrophobic component (R) in the prodrug, at the same time fine tuning the rate and extent of absorption. This prodrug approach has shown to be successful with FDA approved drugs in the market (notable examples: Tenofovir (HIV polymerase inhibitor) and Dabigatran etexilate (thrombin inhibitor). It is envisioned that, following administration and absorption into the bloodstream, the prodrug would undergo hydrolysis (chemical, enzyme-mediated, or spontaneous) to yield intermediate forms (e.g., bisulfite adduct) and subsequently release the active metabolite (e.g., aldehyde). This approach greatly enhances the bioavailability of the active metabolite.

This provides a new approach to improving the therapeutic possibilities for any aldehyde inhibitors of any serine or cysteine protease, as well as α-ketoamides, α-ketoheterocycles, and α-ketoesters, etc. Thus, useful therapeutics can be developed based on this approach, which uses protease inhibitors against caliciviruses, picornaviruses and coronaviruses as proof of concept.

Also described herein is an array of representative mammalian and parasitic protease inhibitors (cathepsin S, cathepsin L, calpain, and falcipain). These salts were demonstrated to display comparable pharmacological activity in vitro and in cell-based systems as the precursor aldehydes by reverting to the aldehyde and bisulfite ion at physiological pH. It was furthermore demonstrated that the bisulfite adduct salts of other transition state inhibitors (e.g., α-ketoamides, α-ketoheterocycles) behave similarly.

In one or more embodiments, a series of ester and carbamate prodrugs of transition state latent inhibitors and transition state mimics (analogues) were synthesized in order to improve their pharmacokinetic and pharmacodynamic properties. The inhibitory activities of the compounds against norovirus 3CL protease in vitro and norovirus in cell replicon cells, were determined. The ester and carbamate prodrugs displayed equivalent potencies as those of the precursor aldehyde bisulfite adducts and precursor aldehydes. The drug-like properties of the inhibitors can be further improved through pegylation. The methodology described herein has wide applicability and can be extended to the bisulfite adducts of common warheads employed in the design of transition state inhibitors of serine and cysteine proteases of medical relevance.

References herein to a "warhead" are used in accordance with common understanding in the art, and denotes the moiety in the inhibitor structure that reacts with the active site cysteine resulting in inactivation of the enzyme. Exemplary applications for this technology include prodrug forms of antivirals against picornaviruses, coronaviruses and caliciviruses, antimalaria agents targeting falcipains, anticancers targeting cathepsins, antiinflammation targeting cathepsins/calpains, neuronal/cardiac protection (such as stroke and heart attack) (cathepsin or calpain target), neuronal diseases such as Alzheimer's and Parkinson's (calpain target), and eye diseases (cataracts and glaucoma—calpain inhibitors).

Thus, in one instance disclosed herein are ester or carbamate prodrug forms of transition state inhibitors or mimics for serine or cysteine proteases. Methods of inhibiting serine or cysteine protease activity are also described herein.

The methods can also be extended to methods of inhibiting viral infection in a subject from one or more viruses selected from the group consisting of caliciviruses, picornaviruses, and/or coronaviruses is also provided. The method comprises administering to the subject a therapeutically-effective amount of a prodrug according to the various embodiments described herein.

Therapeutic or prophylactic compositions are also disclosed. The compositions comprise a first prodrug according to the various embodiments described herein dispersed in a pharmaceutically-acceptable carrier. A kit is also provided herein. The kit comprises: a prodrug according to the various embodiments described herein; and instructions for administering the compound to a subject in need thereof.

A method of preventing or inhibiting replication of a virus in a cell is also disclosed. The method comprises contacting the cell with a prodrug according to the various embodiments described herein, wherein the virus is selected from the group consisting of caliciviruses, picornaviruses, coronaviruses, and combinations thereof.

The invention is also concerned with the use of a prodrug according to the various embodiments described herein to prepare a therapeutic or prophylactic medicament for the treatment or prevention of a viral infection from caliciviruses, picornaviruses, and/or coronaviruses in a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A illustrates the mechanism of action of the ester prodrugs after administration to a subject to release the active metabolite.

FIG. 1B illustrates the mechanism of action of the ester phosphate prodrugs after administration to a subject to release the active metabolite.

FIG. 2A is an image illustrating hydrogen bond interactions of norovirus 3CL protease and precursor aldehyde derived from compound 25. Hydrogen bonds are represented as dashed lines and water mediated contacts are shown as solid lines. The catalytic Cys139 residue is shown covalently bound to the aldehyde warhead carbon.

FIG. 2B is an image of a surface representation of norovirus 3CL protease with inhibitor bound to the active site. Neighboring residues of norovirus 3CL protease are colored yellow (nonpolar), white (weakly polar) and cyan (polar).

FIG. 3A illustrates the reaction schemes for preparing several ester and carbamate prodrug compounds listed in Tables 1 and 2, where DMF: N,N-dimethyl formamide; TLC: thin layer chromatography; EDCI: 1-ethyl-3-(3-dimethylaminopropyl)carbodiimide; HOBt: N-hydroxybenzotriazole; DIEA: diisopropylethylamine; DTT: dithiothreitol; and DMSO: dimethyl sulfoxide.

FIG. 3B illustrates the reaction schemes for preparing several ester and carbamate prodrug compounds listed in Tables 1 and 2 FIG. 4 is a plasma concentration-time profile of compound 25, following PO, SC, and IV administration of compound 11 at 1 mg/kg in rats.

DETAILED DESCRIPTION

The present invention is concerned in one or more embodiments with transition state inhibitors of mammalian, viral, and parasitic serine and cysteine proteases, and specifically (I) ester, (II) carbamate, or (III) ester phosphate prodrug forms thereof:

(I)

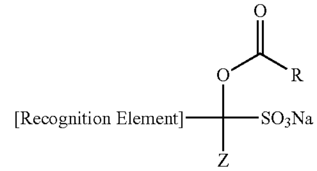

(II)

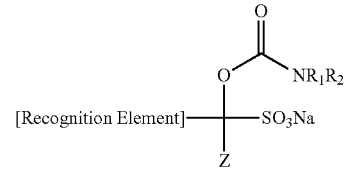

-continued

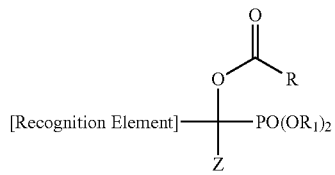
(III)

wherein:
- each Z is —H, —(C=O)NHR$_6$, or —COOR$_6$, where each —R$_6$ is —H, a branched or unbranched alkyl (preferably a C$_1$-C$_8$ alkyl), substituted or unsubstituted phenyls, a substituted or unsubstituted aryl or a substituted or unsubstituted arylalkyl;
- each R is selected from the group consisting of —H, branched and unbranched alkyls (preferably C$_1$-C$_8$ alkyls), substituted or unsubstituted aryls, substituted or unsubstituted arylalkyls, alkoxies, —CHR$_7$NHR$_8$, and —(CH$_2$)$_m$W, where R$_7$ is H or a side chain of a natural or unnatural amino acids, and R$_8$ is —H, a branched or unbranched alkyl (preferably a C$_1$-C$_8$ alkyl), or carboxyalkyl, and where W is —COOR$_6$, —NH$_2$, —NHR$_6$, —NH(C=O)R$_6$, —(C=O)NH$_2$, or —(C=O)NHR$_6$, and m is 1-10 (preferably 2), and each R$_6$ is defined as above;
- each R$_1$ is selected from the group consisting of —H, branched and unbranched alkyls (preferably C$_1$-C$_8$ alkyls), substituted or unsubstituted phenyls, substituted or unsubstituted aryls, substituted or unsubstituted arylalkyls, and halogenated alkyls; and
- each R$_2$ is selected from the group consisting of —H, branched and unbranched alkyls (preferably C$_1$-C$_8$ alkyls), substituted or unsubstituted phenyls, substituted or unsubstituted aryls, substituted or unsubstituted arylalkyls, halogenated alkyls, and —CHR$_7$COOR$_8$, where R$_7$ is H or a side chain of a natural or unnatural amino acid, and R$_8$ is H or a branched or unbranched alkyl (preferably a C$_1$-C$_8$ alkyl).

In the foregoing structures, the "Recognition Element" designates a peptidyl or non-peptidyl moiety in the structure responsible for binding and correct positioning of the inhibitor relative to the active site of the target enzyme, resulting in the reversible formation of the initial enzyme:inhibitor complex. The selectivity of the inhibitor for the targeted enzyme is embodied in the structure of the Recognition Element.

In one or more embodiments, ester, carbamate, or ester phosphate prodrug compounds are described herein, which act as transition state inhibitors of serine or cysteine proteases:

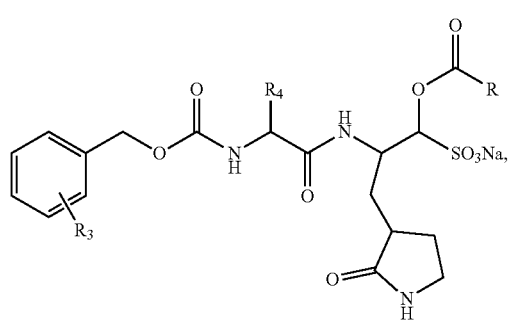
(I)

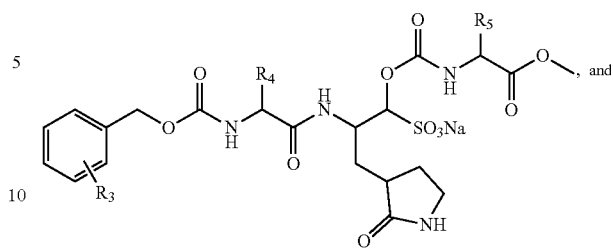
(II)

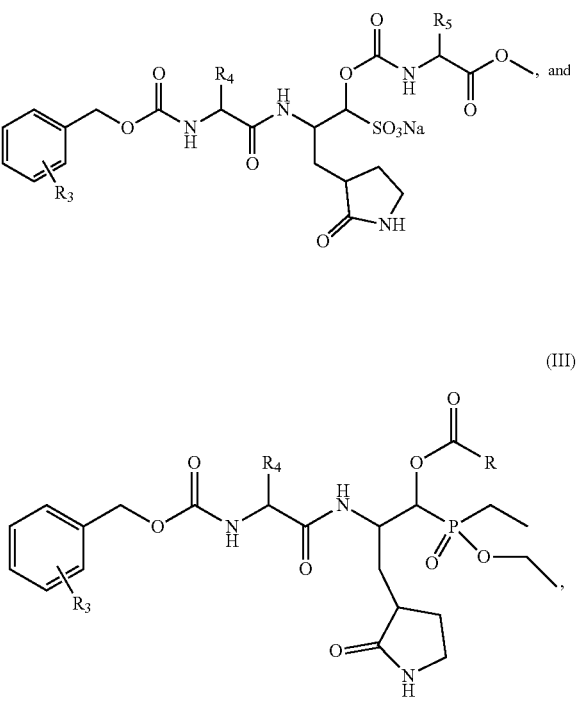
(III)

wherein:
- each R is selected from the group consisting of —H, branched and unbranched alkyls (preferably C$_1$-C$_8$ alkyls), substituted or unsubstituted aryls, substituted or unsubstituted arylalkyls, alkoxies, —CHR$_7$NHR$_8$, and —(CH$_2$)$_m$W, where R$_7$ is H or a side chain of a natural or unnatural amino acids, and R$_8$ is —H, a branched or unbranched alkyl (preferably a C$_1$-C$_8$ alkyl), or carboxyalkyl, and where W is —COOR$_6$, —NH$_2$, —NHR$_6$, —NH(C=O)R$_6$, —(C=O)NH$_2$, or —(C=O)NHR$_6$, and m is 1-10 (preferably 2), and each —R$_6$ is —H, a branched or unbranched alkyl (preferably a C$_1$-C$_8$ alkyl), a substituted or unsubstituted phenyl, a substituted or unsubstituted aryl or a substituted or unsubstituted arylalkyl;
- each R$_3$ is selected from the group consisting of —H, —F (o-, m- and p-positions), —Cl (o-, m- and p-positions), —Br (o-, m- and p-positions), fluoroalkyl, —CN, —OR$_9$, —COOR$_{10}$, and —(C=O)NR$_{10}$R$_{10}$, where R$_9$ is a branched or unbranched alkyl (preferably a C$_1$-C$_8$ alkyl) or fluoroalkyl, and where each R$_{10}$ is H or a branched or unbranched alkyl (preferably a C$_1$-C$_8$ alkyl);
- each R$_4$ is selected from the group consisting of —H, branched and unbranched alkyls (preferably isobutyl), cyclohexylalanine, or other side chain of a natural or unnatural amino acid; and
- each R$_5$ is selected from the group consisting of —H, and a side chain of a natural or unnatural amino acid.

As noted above, the inventive approach to preparing prodrug forms of active compound can be extended to a variety of active agents. In one or more embodiments, the prodrugs are ester- or carbamate-based prodrugs of inhibitors of cathepsin L, cathepsin S, calpains, or falcipain-2:

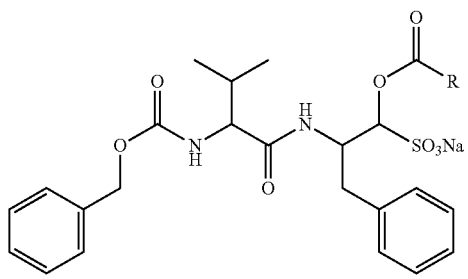

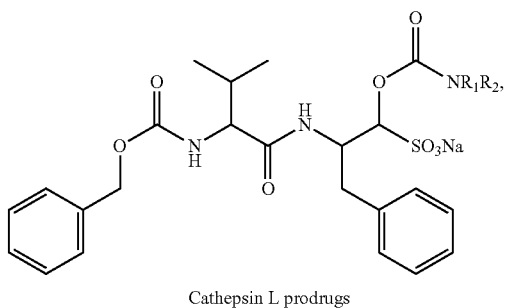

Cathepsin L prodrugs

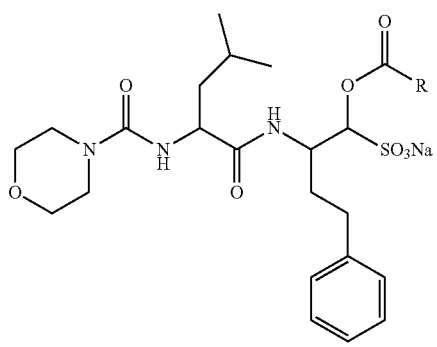

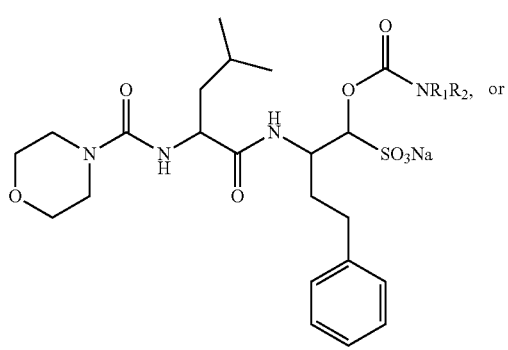

Falcipain-2 & Cathepsin L prodrugs

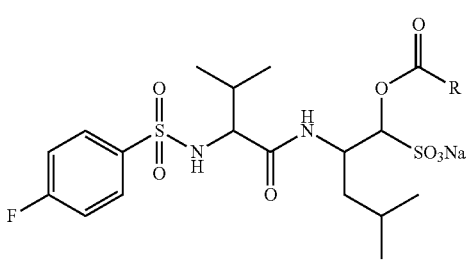

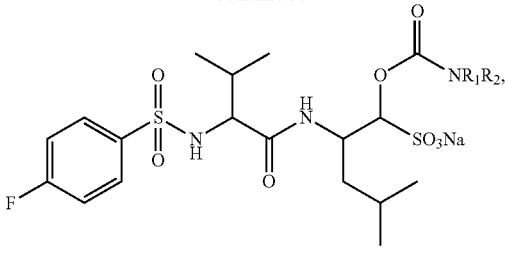

Calpain prodrugs where each R, $R_1$, and $R_2$ is defined as above.

Pharmaceutically acceptable sales of any foregoing compounds can also be used. Combinations of one or more of the foregoing compounds can also be used in the invention. The compounds can also be covalently attached to polyethylene glycol (PEG) to improve pharmacokinetic and pharmacodynamic characteristics. It should be noted that the prodrug mechanism demonstrated here can be extended to other TS inhibitors with warheads beyond sodium bisulfite or aldehyde, such as α-ketoamides. Examples of additional warheads are illustrated by the antiviral compounds described in U.S. Pat. No. 9,474,759, incorporated by reference herein.

Prophylactic and/or therapeutic compositions with specific or broad-spectrum inhibitory activity and/or antiviral activities are also disclosed. The compositions comprise a prodrug compound described herein dispersed in a pharmaceutically-acceptable carrier. The term carrier is used herein to refer to diluents, excipients, vehicles, and the like, in which the prodrug may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the compound or other agents and to minimize any adverse side effects in the subject, as would be well known to one of skill in the art. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), various oil-in-water or water-in-oil emulsions, as well as dimethyl sulfoxide (DMSO), or other acceptable vehicles, and the like.

The composition can comprise a therapeutically effective amount of the prodrug dispersed in the carrier. As used herein, a "therapeutically effective" amount refers to the amount that will elicit the biological or medical response of a tissue, system, or subject that is being sought by a researcher or clinician, and in particular elicit some desired therapeutic or prophylactic effect, such as against the viral infection by preventing and/or inhibiting protease activity and/or viral replication. One of skill in the art recognizes that an amount may be considered therapeutically "effective" even if the condition is not totally eradicated or prevented, but it or its symptoms and/or effects are improved or alleviated partially in the subject. In some embodiments, the composition will comprise from about 5% to about 95% by weight of a prodrug compound described herein, and preferably from about 30% to about 90% by weight of the prodrug compound, based upon the total weight of the composition taken as 100% by weight. In some embodiments, combinations of more than one type of the described prodrug compounds can be included in the composition, in which case the total levels of all such compounds will preferably fall within the ranges described above.

Other ingredients may be included in the composition, such as adjuvants, other active agents, preservatives, buffering agents, salts, other pharmaceutically-acceptable ingredients. The term "adjuvant" is used herein to refer to substances that have immunopotentiating effects and are added to or co-formulated in a therapeutic composition in order to enhance, elicit, and/or modulate the innate, humoral, and/or cell-mediated immune response against the active ingredients. Other active agents that could be included in the composition include other antiviral compounds (e.g., cathepsin inhibitors, polymerase inhibitors such as GS-5734, interferons) or any immunogenic active components (e.g., antigens) such as those that resemble a disease-causing microorganism or infectious agent, and/or are made from weakened or killed forms of the same, its toxins, subunits, particles, and/or one of its surface proteins, such that it provokes an immune response to that microorganism or infectious agent. In addition to live, modified, or attenuated vaccine components, active agents using synthetic peptides, carbohydrates, or antigens can also be used.

Compositions according to the embodiments disclosed herein are useful in inhibiting protease activity. More specifically, the compositions can be used to inhibit viral infection or viral replication, such as by treating and/or preventing viral infection from a variety of causes, including caliciviruses (noroviruses), picornaviruses, and/or coronaviruses in a subject. Viruses in the picornavirus-like supercluster include important human and animal pathogens. For example, caliciviruses include noroviruses (Norwalk virus [NV]), feline calicivirus, MD145, murine norovirus [MNV], vesicular exanthema of swine virus, and rabbit hemorrhagic disease virus. Picornaviruses include enteroviruses (such as enterovirus 71), poliovirus, coxsackievirus, foot-and-mouth disease virus (FMDV), hepatitis A virus (HAV), porcine teschovirus, and rhinovirus (cause of common cold). Coronaviruses include human coronavirus (cause of common cold such as 229E strain), transmissible gastroenteritis virus (TGEV), murine hepatitis virus (MHV), bovine coronavirus (BCV), feline infectious peritonitis virus (FIPV), severe acute respiratory syndrome coronavirus (SARS-Co), and Middle East respiratory syndrome coronavirus (MERS-CoV).

Other conditions that can be targets for treatment through inhibition of protease activity include conditions ameliorated by targeting cathepsins, falcipains, and/or calpains, such as malaria, tumor cells, stroke, heart attack, neural degeneration, cataracts, and glaucoma.

Thus, embodiments described herein have broad-spectrum therapeutic and/or prophylactic uses. The terms "therapeutic" or "treat," as used herein, refer to processes that are intended to produce a beneficial change in an existing condition (e.g., viral infection, disease, disorder) of a subject, such as by reducing the severity of the existing clinical symptoms and/or effects of the infection, and/or reducing the duration of the infection/symptoms/effects. The terms "prophylactic" or "prevent," as used herein, refer to processes that are intended to inhibit or ameliorate the effects of a future infection or disease to which a subject may be exposed (but has no observable signs of current infection). In some cases the composition may prevent the development of observable morbidity from viral infection (i.e., near 100% prevention). In other cases, the composition may only partially prevent and/or lessen the extent of morbidity due to the viral infection (i.e., reduce the severity of the symptoms and/or effects of the infection, and/or reduce the duration of the infection/symptoms/effects). In either case, the compounds are still considered to "prevent" the target infection or disease in the context of the invention.

In use, a therapeutically effective amount of a prodrug compound is administered to a subject. In some embodiments, a composition comprising a therapeutically effective amount of a prodrug compound is administered to a subject. Regardless, the compound or pharmaceutically acceptable salt thereof will preferably be administered to the subject in an amount sufficient to provide antiviral (active) compound levels (independent of salt, if any) of from about 0.1 mg to about 1,000 mg of active metabolite per kg of body weight of the subject, preferably from about 1 mg/kg to about 100 mg/kg of body weight of the subject, and more preferably from about 10 mg/kg to about 50 mg/kg of body weight of the subject. Thus, it will be appreciated that in the case of compound salts, for example, the formulation may be administered in amounts greater than the above ranges to provide sufficient levels of the active compound. In one or more embodiments, treatment protocols include oral or parenteral administration, including intravenous, subcutaneous and intramuscular routes, of the prodrug compound one to four times per day with a total daily dosage of from about 1 to about 200 mg/day per kg of the subject's bodyweight for up to 24 weeks.

Figure 1B:
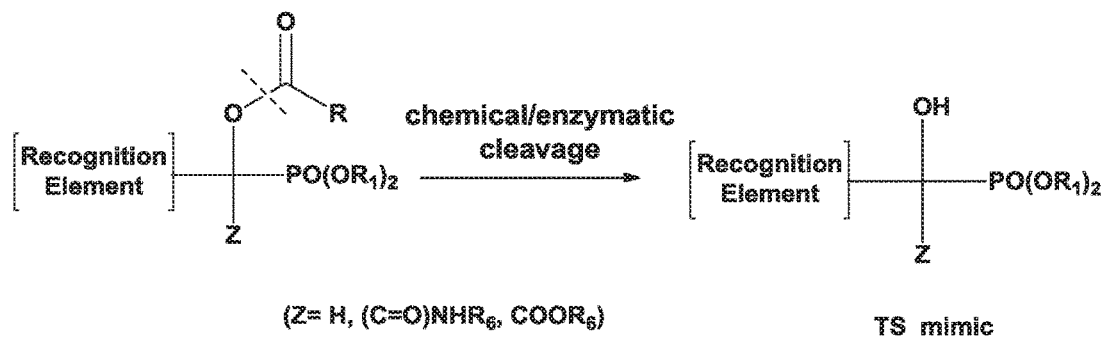
Figure 2A:
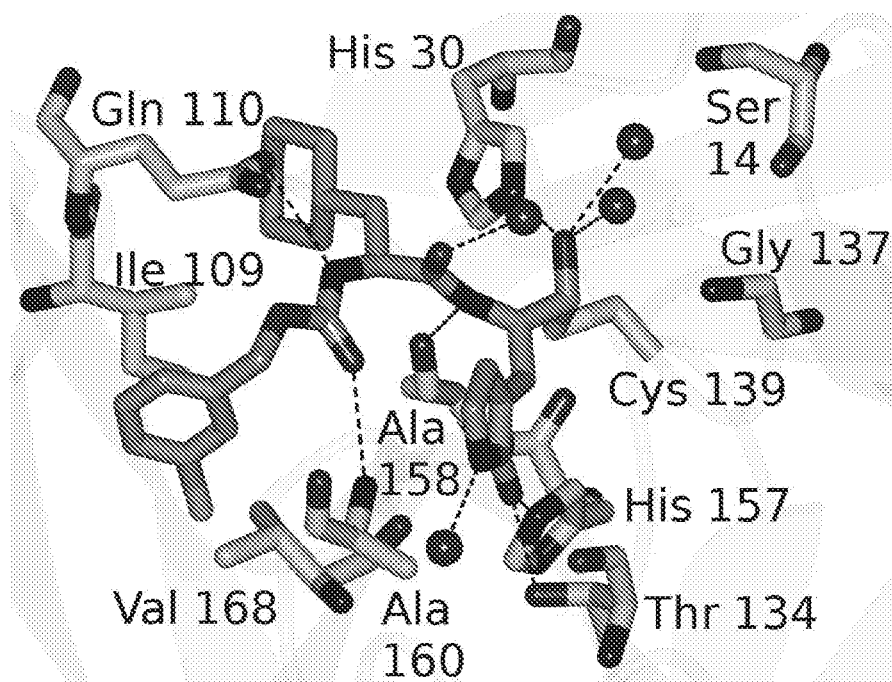
Figure 2B:
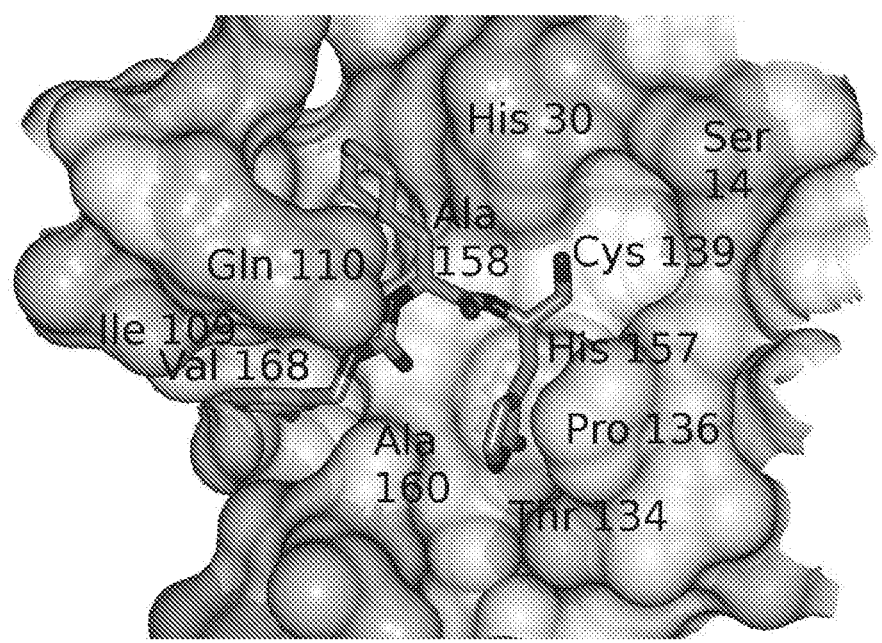

Upon administration, the prodrug mechanism of action entails enzyme-mediated, chemical, or spontaneous degradation or hydrolysis that converts the prodrug into an active metabolite (in some cases involving one or more intermediate compounds). For example, in the case of the bisulfite adducts described herein, the prodrugs I or II are converted into the aldehyde bisulfite adduct which subsequently reverts to the precursor aldehyde (active metabolite), as depicted in FIG. 1A In some cases, intermediate compounds may also have inhibitory activity towards the target, such as by functioning as a transition state mimic (see FIG. 1B). In the case of aldehydes, subsequent reaction with the catalytic cysteine (Cys139) of norovirus 3CLpro leads to inactivation of the enzyme via the formation of a tetrahedral adduct (FIG. 2A-2B). The rate and extent of absorption can be modulated by varying the hydrophobic components and the use of natural and unnatural amino acid side chains. Encapsulation techniques can also be used to facilitate delivery of the prodrug.

In some embodiments, the subject is afflicted with or suffering from a condition (e.g., infection, disease, or disorder) before the compounds are administered, wherein methods described herein are useful for treating the condition and/or ameliorating the effects of the condition. In one or more embodiments, the methods are useful for reversing progression of the disease or condition. In other embodiments, the subject is free of a given condition before administering the compound, wherein the methods described herein are useful for preventing the occurrence or incidence of the condition and/or preventing the effects of the condition, as described above. As noted, the disclosed embodiments are suitable for various routes of administration, depending upon the particular carrier and other ingredients used. For example, the prophylactic and/or therapeutic compounds or compositions can be injected intramuscularly, subcutaneously, intradermally, or intravenously. They can also be administered via mucosa such as intranasally or orally. The compounds or compositions can also be administered through the skin via a transdermal patch.

In some embodiments, the compound or compositions can be provided in unit dosage form in a suitable container. The term "unit dosage form" refers to a physically discrete unit suitable as a unitary dosage for human or animal use. Each unit dosage form may contain a predetermined amount of the inventive compound (and/or other active agents) in the carrier calculated to produce a desired effect. In other embodiments, the compound can be provided separate from the carrier (e.g., in its own vial, ampule, sachet, or other suitable container) for on-site mixing before administration to a subject. A kit comprising the prodrug compound(s) is also disclosed herein. The kit further comprises instructions for administering the compound to a subject. The prodrug compound(s) can be provided as part of a dosage unit, already dispersed in a pharmaceutically-acceptable carrier, or it can be provided separately from the carrier. The kit can further comprise instructions for preparing the prodrug compounds for administration to a subject, including for example, instructions for dispersing the compounds in a suitable carrier.

It will be appreciated that therapeutic and prophylactic methods described herein are applicable to humans as well as any suitable animal, including, without limitation, dogs, cats, and other pets, as well as, rodents, primates, horses, cattle, pigs, etc. The methods can be also applied for clinical research and/or study. Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described and claimed herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

INTRODUCTION

Prior work explored the utilization of bisulfite adducts as a latent form of the warheads used in transition state inhibitors. (See U.S. Pat. No. 9,474,759, incorporated by reference herein with respect to the discussion of such compounds.) The generated bisulfite adducts were found to display comparable pharmacological activity in vitro and in cell-based replicon systems to the precursor aldehydes by reverting to the aldehyde and bisulfite ion at physiological pH. In order to further optimize the PK characteristics of the bisulfite adducts, we report herein the design and use of ester (I) and carbamate (II) prodrug forms of TS inhibitor bisulfite adducts as a specific example to support a general strategy for improving the PK characteristics of TS inhibitors of serine and cysteine proteases (Example 1). We furthermore demonstrate that the same approach can be used with transition state mimics (III) (Example 2).

Example 1

Figure 3A:
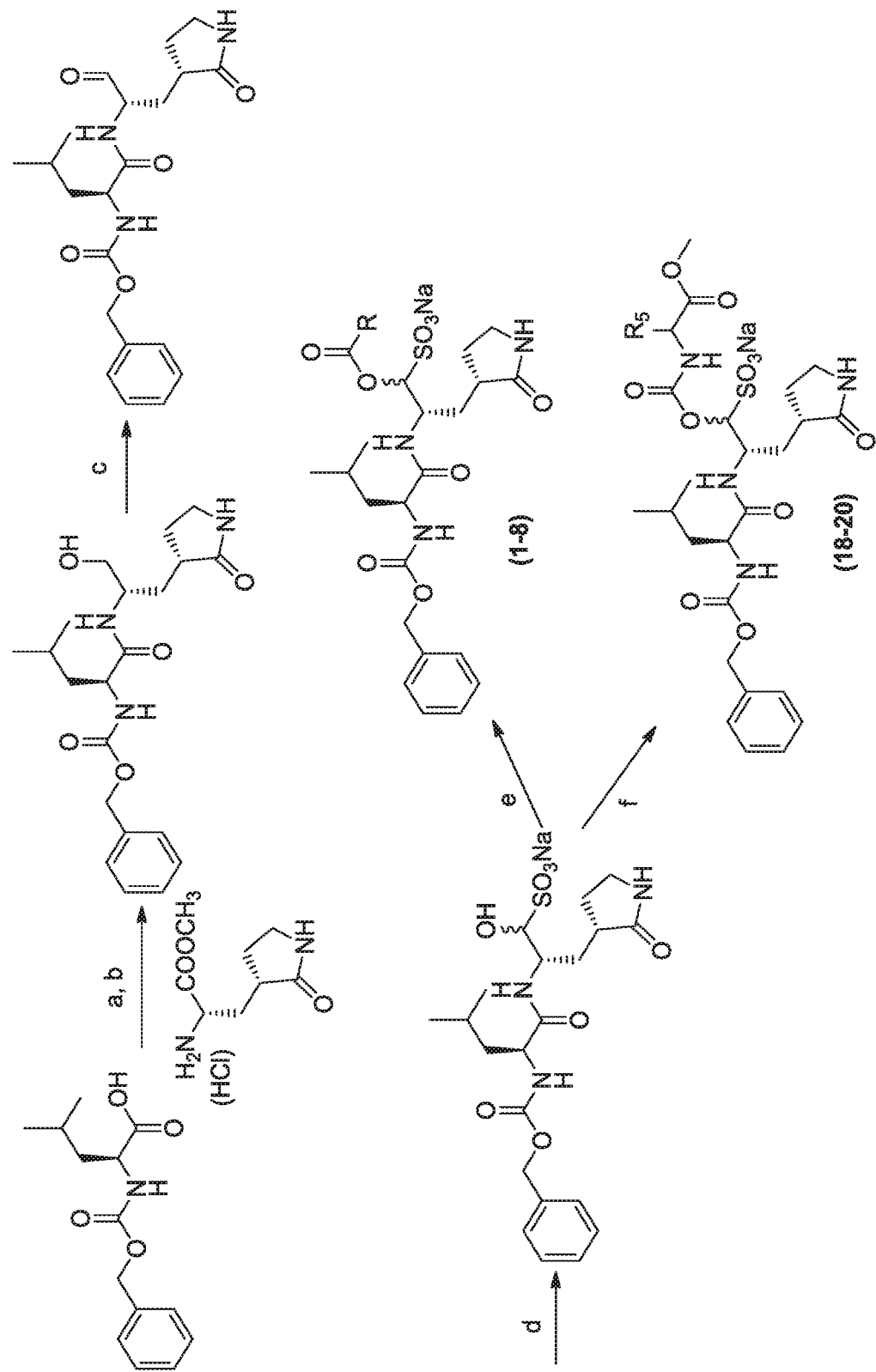
Figure 3B:
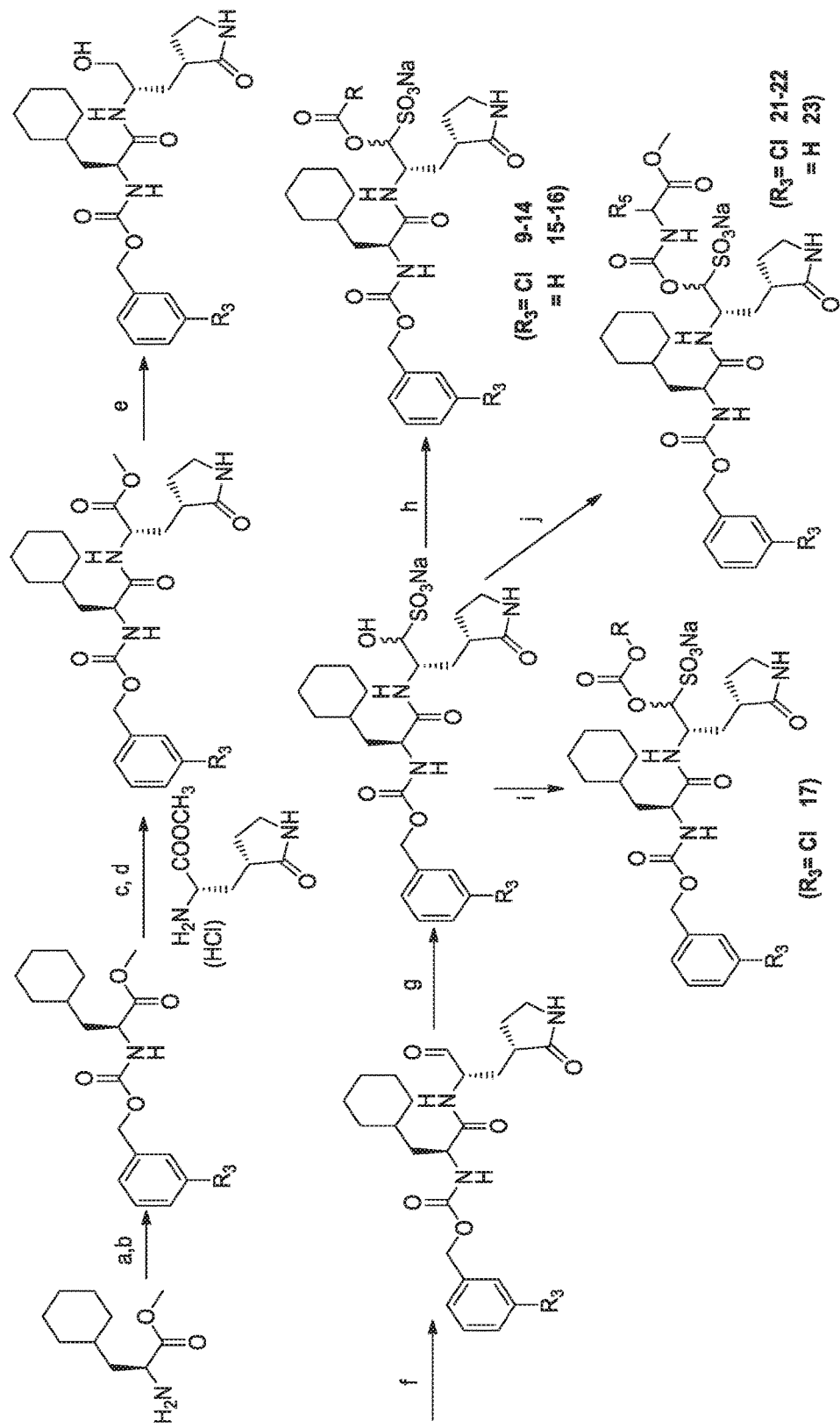

Prodrugs (I-II) were synthesized by refluxing the peptidyl aldehyde bisulfite adduct with an appropriate anhydride, chloroformate or amino acid-derived isocyanate in dry acetonitrile according to the reaction schemes depicted in FIGS. 3A and 3B, with general compound formulas provided below. The pharmacological activity was evaluated as described as is listed in Tables 1-2 below.

TABLE 1

Ester prodrug of peptidyl aldehyde bisulfite adduct (I)

| Compound | $R_3$ | $R_4$ | R | $IC_{50}$ ($\mu M$)* | $EC_{50}$ ($\mu M$)** |
|---|---|---|---|---|---|
| 1 | H | Isobutyl | $CH_3$ | 10.5 | 0.6 |
| 2 | | | $CH_2CH_3$ | 7.5 | 0.7 |
| 3 | | | $(CH_2)_2CH_3$ | 3.7 | 1.3 |
| 4 | | | $(CH_2)_3CH_3$ | 3.5 | 1.4 |
| 5 | | | $(CH_2)_4CH_3$ | 2.8 | 0.3 |
| 6 | | | $(CH_2)_6CH_3$ | 3.0 | 0.5 |
| 7 | | | $C_6H_5$ | 7.2 | 0.8 |
| 8 | | | $CH(CH_3)_2$ | 3.5 | 0.3 |
| 9 | m-Cl | Cyclohexyl-alanine | $CH_3$ | 0.08 | 0.03 |
| 10 | | | $CH_2CH_3$ | 0.1 | 0.025 |
| 11 | | | $(CH_2)_4CH_3$ | 0.1 | 0.015 |
| 12 | | | $(CH_2)_6CH_3$ | 0.9 | 0.03 |
| 13 | | | $CH(CH_3)_2$ | 0.3 | 0.03 |
| 14 | | | $C_6H_{11}$ | 0.4 | 0.02 |
| 15 | H | | $CH_3$ | 7.5 | 0.2 |
| 16 | | | $(CH_2)_4CH_3$ | 0.6 | 0.06 |
| 17 | m-Cl | | $O(CH_2)_5CH_3$ | 0.8 | 0.025 |

*50% inhibitory concentration in the enzyme assay
**50% effective concentration in cell culture

TABLE 2

Carbamate prodrug of peptidyl aldehyde bisulfite adduct (II)

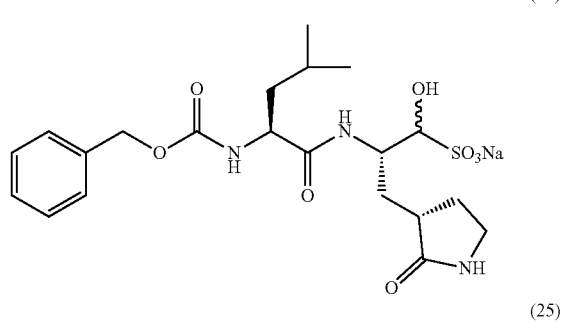

| Compound | $R_3$ | $R_4$ | $R_5$ | IC$_{50}$ (µM) | EC$_{50}$ (µM) |
|---|---|---|---|---|---|
| 18 | H | Isobutyl | H | 3.1 | 0.4 |
| 19 | | | CH$_3$ | 1.8 | 0.3 |
| 20 | | | CH(CH$_3$)$_2$ | 2.5 | 0.4 |
| 21 | m-Cl | Cyclohexyl-alanine | CH$_3$ | 0.8 | 0.025 |
| 22 | | | CH(CH$_3$)$_2$ | 0.5 | 0.04 |
| 23 | H | | CH$_3$ | 10.2 | 0.2 |

Control or baseline sodium bisulfite adducts and aldehyde compounds were used for comparison to the prodrug forms:

(24)

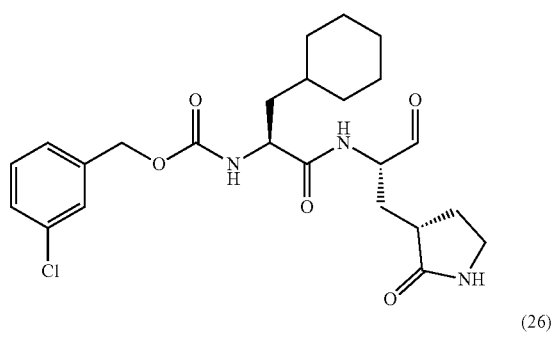

(25)

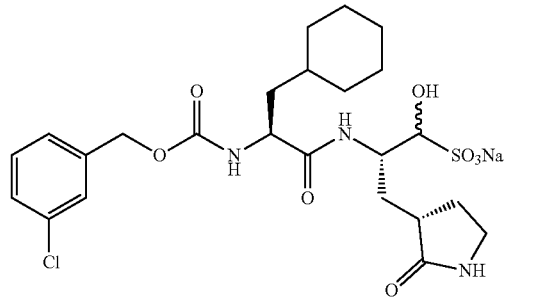

(26)

Sodium bisulfite adduct 24 had an IC$_{50}$ 0.8 µM and an EC$_{50}$ 0.3 M. Aldehyde compound 25 had an IC$_{50}$ 0.1 M and an EC$_{50}$ 0.02 µM. Chloro-substituted bisulfite adduct 26 had an IC$_{50}$ 0.1 µM and an EC$_{50}$ 0.02 M.

Materials and Methods

General.

Reagents and dry solvents were purchased from various chemical suppliers (Aldrich, Acros Organics, Chem-Impex, TCI America, Oakwood chemicals, Bachem, and Fisher) and were used as obtained. Silica gel (230-450 mesh) used for flash chromatography was purchased from Sorbent Technologies (Atlanta, Ga.). The $^1$H spectra were recorded in CDCl$_3$ or DMSO-d$_6$ on a Varian XL-400 NMR spectrometer. High resolution mass spectra (HRMS) were performed at the University of Kansas Mass Spectrometry lab using an LCT Premier mass spectrometer (Waters, Milford, Mass.) equipped with a time of flight mass analyzer and an electrospray ion source. Thin layer chromatography was performed using Analtech silica gel plates and visualization was accomplished using UV light and/or iodine. The purity of the compounds was determined by high-performance liquid chromatography (HPLC) using a Varian Pro-star HPLC system with a normal phase column (Kinetex 2.6 u HILIC 100 A, 75×4.6 mm) at 254 nm. Analysis was conducted using two different methods. Method A: isocratic with 40% acetonitrile and 60% dichloromethane, mobile phase flow rate 1.0 mL/min. Method B: isocratic with 20% acetonitrile and 80% dichloromethane, mobile phase flow rate 1.0 mL/min. All final compounds had a purity of ≥95% by both methods.

Synthesis of compounds 1-15: General Procedure. Alkanoic anhydride (1 mmol) was added to a solution of dipeptidyl bisulfite salt (1 mmol) in dry acetonitrile 10 mL and the reaction mixture was refluxed for 2 h with stirring. The solvent was removed in vacuo. The residue was washed thoroughly with ethyl ether until a white precipitate formed. The supernatant was carefully removed using pipette and the white precipitate was dried in vacuo.

(5S,8S)-5-Isobutyl-3,6,11-trioxo-8-(((S)-2-oxopyrrolidin-3-yl)methyl)-1-phenyl-2,10-dioxa-4,7-diazadodecane-9-sulfonate (1). Yield (67%), mp 94-97° C. $^1$H NMR (400 MHz, DMSO-d$_6$) δ ppm 7.86-7.93 (m, 1H), 7.62-7.71 (m, 1H), 7.48 (br. s., 1H), 7.23-7.40 (m, 5H), 5.30 (d, J=2.34 Hz, 1H), 4.96-5.07 (m, 2H), 4.08-4.20 (m, 1H), 3.93 (d, J=8.30 Hz, 1H), 3.09 (br. s., 2H), 2.05-2.20 (m, 1H), 2.02 (s, 3H), 1.87-1.95 (m, 2H), 1.66-1.73 (m, 1H), 1.51-1.64 (m, 2H), 1.27-1.49 (m, 2H), 0.79-0.88 (m, 6H). HRMS (ESI) calcd for C$_{23}$H$_{32}$N$_3$O$_9$S: [M−]: 526.1865. Found: 526.1857. HPLC purity 96.4% (Method A).

(5S,8S)-5-Isobutyl-3,6,11-trioxo-8-(((S)-2-oxopyrrolidin-3-yl)methyl)-1-phenyl-2,10-dioxa-4,7-diazatridecane-9-sulfonate (2). Yield (63%), mp 83-85° C. $^1$H NMR (400 MHz, DMSO-d$_6$) δ ppm 7.83-7.91 (m, 1H), 7.55 (t, J=7.62 Hz, 1H), 7.45-7.51 (m, 1H), 7.35 (d, J=4.30 Hz, 5H), 5.58-5.67 (m, 1H), 4.93-5.08 (m, 2H), 4.14-4.28 (m, 1H), 3.90-4.12 (m, 1H), 2.93-3.19 (m, 2H), 2.00-2.26 (m, 2H), 1.83-1.96 (m, 1H), 1.74-1.82 (m, 2H), 1.54-1.71 (m, 4H), 1.31-1.52 (m, 1H), 0.95 (t, J=7.42 Hz, 3H), 0.75-0.90 (m, 6H). HRMS (ESI) calcd for C$_{24}$H$_{34}$N$_3$O$_9$S: [M−]: 540.2021. Found: 540.2013. HPLC purity 95.8% (Method A).

(5S,8S)-5-Isobutyl-3,6,11-trioxo-8-(((S)-2-oxopyrrolidin-3-yl)methyl)-1-phenyl-2,10-dioxa-4,7-diazatetradecane-9-sulfonate (3): Yield (68%), mp 77-79° C. $^1$H NMR (400 MHz, DMSO-d$_6$) δ ppm 8.60-8.66 (m, 1H), 8.49-8.55 (m, 1H), 7.62-7.71 (m, 1H), 7.26-7.57 (m, 5H), 5.60-5.68 (m, 1H), 4.94-5.18 (m, 2H), 3.83-4.05 (m, 1H), 3.74 (d, J=7.03 Hz, 1H), 2.98-3.18 (m, 2H), 2.12 (br. s., 2H), 1.99

(br. s., 1H), 1.60 (br. s., 3H), 1.46 (d, J=7.23 Hz, 6H), 1.11 (t, J=6.74 Hz, 3H), 0.85 (br. s., 6H). HRMS (ESI) calcd for $C_{25}H_{36}N_3O_9S$: [M–]: 554.2178. Found: 554.2166. HPLC purity 98.2% (Method A).

(5S,8S)-5-Isobutyl-3,6,11-trioxo-8-(((S)-2-oxopyrrolidin-3-yl)methyl)-1-phenyl-2,10-dioxa-4,7-diazapentadecane-9-sulfonate (4): Yield (52%), mp 80-83° C. $^1$H NMR (400 MHz, DMSO-$d_6$) δ ppm 8.45-8.51 (m, 1H), 7.61-7.66 (m, 1H), 7.44-7.53 (m, 1H), 7.35 (br. s., 5H), 5.10-5.15 (m, 1H), 4.98-5.07 (m, 2H), 4.17-4.26 (m, 1H), 4.03-4.13 (m, 1H), 3.00-3.17 (m, 2H), 2.16-2.22 (m, 2H), 1.86-1.94 (br. s., 1H), 1.60-1.70 (m, 2H), 1.43-1.54 (m, 4H), 1.23-1.35 (m, 5H), 1.10 (t, J=7.78 Hz, 3H), 0.80-0.91 (m, 6H). HRMS (ESI) calcd for $C_{26}H_{38}N_3O_9S$: [M–]: 568.2334. Found: 568.2336. HPLC purity 94.7% (Method A).

(5 S, 8S)-5-Isobutyl-3,6,11-trioxo-8-(((S)-2-oxopyrrolidin-3-yl)methyl)-1-phenyl-2,10-dioxa-4,7-diazahexadecane-9-sulfonate (5): Yield (62%), mp 72-75° C. $^1$H NMR (400 MHz, DMSO-$d_6$) δ ppm 7.58-7.68 (m, 1H), 7.50 (d, J=8.20 Hz, 1H), 7.44 (d, J=3.91 Hz, 1H), 7.28-7.40 (m, 5H), 5.06 (s, 1H), 4.99-5.04 (m, 2H), 3.91-4.00 (m, 1H), 3.81-3.85 (m, 1H), 2.97-3.15 (m, 2H), 2.07-2.20 (m, 2H), 1.87-1.91 (m, 1H), 1.57-1.64 (m, 2H), 1.40-1.49 (m, 7H), 1.28 (br. s., 4H), 1.10 (t, J=6.20 Hz, 3H), 0.80-0.91 (m, 6H). HRMS (ESI) calcd for $C_{27}H_{40}N_3O_9S$: [M–]: 582.2491. Found: 582.2487. HPLC purity 97.2% (Method A).

(5S,8S)-5-Isobutyl-3,6,11-trioxo-8-(((S)-2-oxopyrrolidin-3-yl)methyl)-1-phenyl-2,10-dioxa-4,7-diazaoctadecane-9-sulfonate (6): Yield (61%), mp 74-77° C. $^1$H NMR (400 MHz, DMSO-$d_6$) δ ppm 8.45-8.51 (m, 1H), 7.62-7.66 (m, 1H), 7.46-7.54 (m, 1H), 7.28-7.42 (m, 5H), 5.31-5.34 (m, 1H), 4.96-5.06 (m, 2H), 4.16-4.22 (m, 1H), 4.05-4.11 (m, 1H), 3.00-3.17 (m, 2H), 2.09-2.20 (m, 5H), 1.40-1.54 (m, 6H), 1.20-1.32 (m, 9H), 1.11 (t, J=6.70 Hz, 3H), 0.86 (br. s., 6H). HRMS (ESI) calcd for $C_{29}H_{44}N_3O_9S$: [M–]: 610.2804. Found: 610.2817. HPLC purity 95.8% (Method A).

(5S,8S)-5-Isobutyl-3,6,11-trioxo-8-(((S)-2-oxopyrrolidin-3-yl)methyl)-1,11-diphenyl-2,10-dioxa-4,7-diazaundecane-9-sulfonate (7): Yield (51%), mp 84-87° C. $^1$H NMR (400 MHz, DMSO-$d_6$) δ ppm 8.51-8.56 (m, 1H), 8.15 (d, J=7.13 Hz, 1H), 7.93 (d, J=7.03 Hz, 2H), 7.60-7.70 (m, 1H), 7.46-7.57 (m, 3H), 7.25-7.43 (m, 5H), 5.33-5.38 (m, 1H), 4.97-5.09 (m, 2H), 4.14-4.35 (m, 1H), 3.82-4.11 (m, 1H), 2.93-3.20 (m, 2H), 1.97-2.35 (m, 3H), 1.74-1.95 (m, 1H), 1.54-1.69 (m, 2H), 1.28-1.51 (m, 2H), 0.74-0.92 (m, 6H). HRMS (ESI) calcd for $C_{28}H_{34}N_3O_9S$: [M–]: 588.2021. Found: 588.2017. HPLC purity 96.7% (Method A).

(5S,8S)-5-Isobutyl-12-methyl-3,6,11-trioxo-8-(((S)-2-oxopyrrolidin-3-yl)methyl)-1-phenyl-2,10-dioxa-4,7-diazatridecane-9-sulfonate (8): Yield (69%), mp 71-73° C. $^1$H NMR (400 MHz, DMSO-$d_6$) δ ppm 8.46-8.52 (m, 1H), 7.59-7.63 (m, 1H), 7.46-7.54 (m, 1H), 7.32 (d, J=1.56 Hz, 5H), 4.93-5.05 (m, 3H), 4.14-4.23 (m, 1H), 4.01-4.08 (m, 1H), 3.27-3.38 (m, 2H), 3.03-3.12 (m, 2H), 2.11-2.21 (m, 1H), 1.52-1.65 (m, 2H), 1.38-1.50 (m, 2H), 1.01-1.12 (m, 2H), 0.95 (d, J=6.93 Hz, 6H), 0.84 (d, J=7.23 Hz, 6H). HRMS (ESI) calcd for $C_{25}H_{36}N_3O_9S$: [M–]: 554.2178. Found: 554.2158. HPLC purity 94.6% (Method A).

(5 S, 8S)-1-(3-Chlorophenyl)-5-(cyclohexylmethyl)-3,6,11-trioxo-8-(((S)-2-oxopyrrolidin-3-yl)methyl)-2,10-dioxa-4,7-diazadodecane-9-sulfonate (9): Yield (69%), mp 94-96° C. $^1$H NMR (400 MHz, DMSO-$d_6$) δ ppm 8.46-8.52 (m, 1H), 7.61-7.64 (m, 1H), 7.54-7.58 (m, 1H), 7.46-7.51 (m, 1H), 7.34-7.43 (m, 1H), 7.27-7.32 (m, 1H), 5.28-5.32 (m, 1H), 5.04 (d, J=5.66 Hz, 2H), 4.14-4.22 (m, 1H), 4.06-4.13 (m, 1H), 3.01-3.20 (m, 2H), 2.22-2.36 (m, 1H), 1.99-2.19 (m, 4H), 1.97 (s, 3H), 1.54-1.74 (m, 6H), 1.49 (br. s., 1H), 1.06-1.21 (m, 4H), 0.76-0.96 (m, 2H). HRMS (ESI) calcd for $C_{26}H_{35}ClN_3O_9S$: [M–]: 600.1788. Found: 600.1719. HPLC purity 98.3% (Method A).

(5 S, 8S)-1-(3-chlorophenyl)-5-(cyclohexylmethyl)-3,6,11-trioxo-8-((2-oxopyrrolidin-3-yl)methyl)-2,10-dioxa-4,7-diazatridecane-9-sulfonate (10): Yield (75%), mp 74-77° C. $^1$H NMR (400 MHz, DMSO-$d_6$) δ ppm 8.47-8.52 (m, 1H), 7.74-7.79 (m, 1H), 7.66 (d, J=8.40 Hz, 1H), 7.49 (d, J=8.98 Hz, 1H), 7.33-7.45 (m, 2H), 7.29 (br. s., 1H), 5.03 (br. s., 2H), 4.67 (br. s., 1H), 4.01 (d, J=6.44 Hz, 1H), 3.68-3.79 (m, 1H), 3.09 (d, J=8.40 Hz, 2H), 2.99 (d, J=7.81 Hz, 2H), 2.17-2.30 (m, 2H), 2.10 (br. s., 2H), 1.74-1.84 (m, 1H), 1.48-1.72 (m, 4H), 1.34-1.46 (m, 2H), 1.30 (d, J=6.05 Hz, 1H), 0.95-1.16 (m, 6H), ppm 0.85 (br. s., 3H). HRMS (ESI) calcd for $C_{27}H_{37}ClN_3O_9S$: [M–]: 614.1912. Found: 614.1947. HPLC purity 98.2% (Method A).

(5S,8S)-1-(3-Chlorophenyl)-5-(cyclohexylmethyl)-3,6,11-trioxo-8-(((S)-2-oxopyrrolidin-3-yl)methyl)-2,10-dioxa-4,7-diazahexadecane-9-sulfonate (11): Yield (71%), mp 72-74° C. $^1$H NMR (400 MHz, DMSO-$d_6$) δ ppm 8.52 (d, J=7.71 Hz, 1H), 7.68 (s, 1H), 7.57 (dd, J=3.91, 7.91 Hz, 1H), 7.49 (d, J=8.89 Hz, 1H), 7.34-7.47 (m, 2H), 7.31 (d, J=6.54 Hz, 1H), 5.32-5.35 (m, 1H), 4.98-5.08 (m, 2H), 4.15-4.28 (m, 1H), 3.90-4.13 (m, 1H), 2.97-3.19 (m, 2H), 2.03-2.28 (m, 4H), 1.87-1.96 (m, 2H), 1.62 (d, J=8.59 Hz, 7H), 1.39-1.52 (m, 4H), 1.21-1.35 (m, 6H), 1.05-1.15 (m, 4H), 0.81-0.93 (m, 2H). HRMS (ESI) calcd for $C_{30}H_{43}ClN_3O_9S$: [M–]: 656.2414. Found: 656.2403. HPLC purity 98.9% (Method A).

(5 S, 8S)-1-(3-Chlorophenyl)-5-(cyclohexylmethyl)-3,6,11-trioxo-8-(((S)-2-oxopyrrolidin-3-yl)methyl)-2,10-dioxa-4,7-diazaoctadecane-9-sulfonate (12): Yield (71%), mp 71-73° C. $^1$H NMR (400 MHz, DMSO-$d_6$) δ ppm 8.47 (d, J=7.41 Hz, 1H), 7.53-7.62 (m, 1H), 7.49 (d, J=8.49 Hz, 2H), 7.33-7.46 (m, 3H), 5.06 (br. s., 1H), 5.03 (s, 2H), 4.07-4.18 (m, 1H), 3.81-3.87 (m, 1H), 2.97-3.14 (m, 2H), 2.33 (br. s, 4H), 1.63 (d, J=6.25 Hz, 6H), 1.38-1.47 (m, 4H), 1.19-1.31 (m, 10H), 1.10 (td, J=7.10, 7.50 Hz, 6H), 0.86 (t, J=6.54 Hz, 3H). HRMS (ESI) calcd for $C_{32}H_{47}ClN_3O_9S$: [M–]: 684.2727. Found: 684.2706. HPLC purity 97.3% (Method A).

(5 S, 8S)-1-(3-Chlorophenyl)-5-(cyclohexylmethyl)-12-methyl-3,6,11-trioxo-8-(((S)-2-oxopyrrolidin-3-yl)methyl)-2,10-dioxa-4,7-diazatridecane-9-sulfonate (13): Yield (41%), mp 76-78° C. $^1$H NMR (400 MHz, DMSO-$d_6$) δ ppm 8.50 (d, J=7.71 Hz, 1H), 7.62 (s, 1H), 7.56 (d, J=7.71 Hz, 1H), 7.34-7.45 (m, 3H), 7.30 (d, J=4.59 Hz, 1H), 5.33-5.39 (m, 1H), 5.04 (d, J=4.98 Hz, 2H), 4.15-4.23 (m, 1H), 4.10 (q, J=7.94 Hz, 1H), 3.01-3.18 (m, 2H), 2.08-2.27 (m, 1H), 1.84-1.95 (m, 2H), 1.56-1.76 (m, 8H), 1.44-1.52 (m, 2H), 1.09-1.17 (m, 4H), 1.06 (d, J=6.93 Hz, 6H), 0.82-0.93 (m, 2H). HRMS (ESI) calcd for $C_{28}H_{39}ClN_3O_9S$: [M–]: 628.2101. Found: 628.2115. HPLC purity 95.8% (Method A).

(5 S,8S)-1-(3-Chlorophenyl)-11-cyclohexyl-5-(cyclohexylmethyl)-3,6,11-trioxo-8-(((S)-2-oxopyrrolidin-3-yl)methyl)-2,10-dioxa-4,7-diazaundecane-9-sulfonate (14): Yield (53%), mp 86-88° C. $^1$H NMR (400 MHz, DMSO-$d_6$) δ ppm 8.48-8.52 (m, 1H), 7.50 (d, J=8.20 Hz, 1H), 7.44 (d, J=3.91 Hz, 1H), 7.28-7.40 (m, 4H), 5.06 (s, 1H), 4.99-5.04 (m, 2H), 3.91-4.00 (m, 1H), 3.81-3.85 (m, 1H), 2.97-3.15 (m, 2H), 2.07-2.20 (m, 4H), 1.87-1.91 (m, 2H), 1.57-1.64 (m, 2H), 1.40-1.49 (m, 5H), 1.28 (s, 4H), 1.10 (td, J=6.20, 6.50 Hz, 4H), 0.80-0.91 (m, 8H). HRMS (ESI) calcd for $C_{31}H_{43}ClN_3O_9S$: [M–]: 668.2414. Found: 668.2403. HPLC purity 97.7% (Method A).

(5S,8S)-5-(Cyclohexylmethyl)-3,6,11-trioxo-8-(((S)-2-oxopyrrolidin-3-yl)methyl)-1-phenyl-2,10-dioxa-4,7-diazadodecane-9-sulfonate (15): Yield (62%), mp 92-94° C. $^1$H NMR (400 MHz, DMSO-$d_6$) δ ppm 8.34 (d, J=8.79 Hz, 1H), 7.47-7.53 (m, 1H), 7.34 (br. s., 5H), 5.68-5.76 (m, 1H), 5.02 (s, 2H), 4.64-4.71 (m, 1H), 3.97-4.09 (m, 1H), 3.73 (q, J=7.13 Hz, 1H), 2.96-3.15 (m, 2H), 2.04-2.26 (m, 2H), 1.99 (s, 3H), 1.79 (d, J=11.03 Hz, 2H), 1.53-1.72 (m, 6H), 1.38-1.48 (m, 3H), 1.22-1.34 (m, 1H), 1.04-1.20 (m, 2H), 0.86 (d, J=11.33 Hz, 2H). HRMS (ESI) calcd for $C_{26}H_{36}N_3O_9S$: [M−]: 566.2178. Found: 566.2147. HPLC purity 95.8% (Method A).

(5S,8S)-11-Cyclohexyl-5-(cyclohexylmethyl)-3,6,11-trioxo-8-(((S)-2-oxopyrrolidin-3-yl)methyl)-1-phenyl-2,10-dioxa-4,7-diazaundecane-9-sulfonate (16): Yield (52%), mp 83-85° C. $^1$H NMR (400 MHz, DMSO-$d_6$) δ ppm 8.43-8.52 (m, 1H), 7.64 (d, J=8.49 Hz, 1H), 7.48-7.54 (m, 1H), 7.34 (br. s., 5H), 5.69-5.76 (m, 1H), 5.02 (s, 2H), 3.96-4.12 (m, 1H), 3.69-3.81 (m, 1H), 2.96-3.17 (m, 2H), 2.18 (t, J=7.37 Hz, 4H), 2.13 (br. s., 2H), 1.48-1.71 (m, 7H), 1.35-1.46 (m, 2H), 1.27 (d, J=4.00 Hz, 4H), 1.04-1.19 (m, 4H), 0.85 (qd, J=5.20, 5.60 Hz, 6H). HRMS (ESI) calcd for $C_{26}H_{36}N_3O_9S$: [M−]: 634.2804. Found: 634.2818. HPLC purity 98.1% (Method A).

Synthesis of compound 17: General procedure. Hexyl chloroformate (1.1 mmol) was added to a solution of dipeptidyl bisulfite salt (1 mmol) in dry acetonitrile (10 mL) and the reaction mixture was refluxed for 2 h with stirring. The solvent was removed in vacuo and the oily residue was treated with ether/hexane until a white precipitate formed. The supernatant was carefully removed using a pipette and the white solid was dried in vacuo.

(5 S, 8S)-1-(3-chlorophenyl)-5-(cyclohexylmethyl)-3,6,11-trioxo-8-((2-oxo-pyrrolidin-3-yl)methyl)-2,10,12-trioxa-4,7-diazaoctadecane-9-sulfonate (17): Yield (61%), mp 77-79° C. $^1$H NMR (400 MHz, DMSO-$d_6$) δ ppm 8.53 (d, J=7.74 Hz, 1H), 7.68 (s, 1H), 7.57 (dd, J=3.91, 7.91 Hz, 1H), 7.49 (d, J=8.89 Hz, 1H), 7.34-7.47 (m, 2H), 7.31 (d, J=6.54 Hz, 1H), 5.32-5.35 (m, 1H), 4.98-5.08 (m, 2H), 4.15-4.28 (m, 1H), 3.90-4.13 (m, 1H), 3.60 (t, J=8.54 Hz, 2H), 2.97-3.19 (m, 2H), 2.03-2.28 (m, 4H), 1.87-1.96 (m, 2H), 1.62 (d, J=8.59 Hz, 7H), 1.39-1.52 (m, 4H), 1.21-1.35 (m, 6H), 1.05-1.15 (m, 4H), 0.81-0.93 (m, 2H). HRMS (ESI) calcd for $C_{31}H_{45}ClN_3O_{10}S$: [M−]: 709.2412. Found: 709.2408. HPLC purity 98.9% (Method A).

Synthesis of compounds 18-21: General procedure. Isocyanate of amino acid (1.1 mmol) was added to a solution of dipeptidyl bisulfite salt (1 mmol) in dry acetonitrile (10 mL) and the reaction mixture was refluxed for 2 h with stirring. The solvent was removed in vacuo and the oily residue was treated with ether until a white precipitate formed. The supernatant was carefully removed using a pipette and the white solid was dried in vacuo.

(5 S,8S)-5-Isobutyl-3,6,11,14-tetraoxo-8-(((S)-2-oxopyrrolidin-3-yl)methyl)-1-phenyl-2,10,15-trioxa-4,7,12-triazahexadecane-9-sulfonate (18): Yield (67%), mp 83-86° C. $^1$H NMR (400 MHz, DMSO-$d_6$) δ ppm 8.43 (d, J=8.31 Hz, 1H), 7.59 (s, 1H), 7.40-7.52 (m, 1H), 7.28-7.37 (m, 5H), 6.48 (t, J=6.91 Hz, 1H), 4.98-5.07 (m, 2H), 4.15-4.28 (m, 1H), 3.87-4.03 (m, 1H), 3.74 (s, 3H), 3.68 (d, J=7.13 Hz, 1H), 3.35 (d, J=7.03 Hz, 1H), 3.11 (dd, J=8.84, 18.43 Hz, 2H), 2.02-2.26 (m, 2H), 1.53-1.74 (m, 2H), 1.37-1.54 (m, 3H), 1.05-1.16 (m, 2H), 0.86 (d, J=7.33 Hz, 6H).HRMS (ESI) calcd for $C_{25}H_{35}N_4O_{11}S$: [M−]: 599.2029. Found: 599.2019. HPLC purity 96.3% (Method B).

(5 S,8S)-5-Isobutyl-13-methyl-3,6,11,14-tetraoxo-8-(((S)-2-oxopyrrolidin-3-yl) methyl)-1-phenyl-2,10,15-trioxa-4,7,12-triazahexadecane-9-sulfonate (19): Yield (70%), mp 63-65° C. $^1$H NMR (400 MHz, DMSO-$d_6$) δ ppm 8.45 (d, J=7.52 Hz, 1H), 7.60 (s, 1H), 7.46 (d, J=7.81 Hz, 1H), 7.28-7.37 (m, 5H), 6.39 (d, J=7.62 Hz, 1H), 5.01 (s, 2H), 4.34-4.41 (m, 1H), 4.13-4.25 (m, 1H), 4.06 (q, J=7.20 Hz, 1H), 3.72 (s, 3H), 3.00-3.16 (m, 2H), 2.26 (dd, J=3.66, 9.03 Hz, 1H), 1.87 (ddd, J=4.05, 10.69, 14.35 Hz, 2H), 1.54-1.67 (m, 3H), 1.38-1.49 (m, 2H), 1.21 (d, J=7.32 Hz, 3H), 1.07 (dt, J=4.39, 7.08 Hz, 1H), 0.84 (d, J=7.60 Hz, 6H). HRMS (ESI) calcd for $C_{26}H_{37}N_4O_{11}S$: [M−]: 613.2185. Found: 613.2174. HPLC purity 95.9% (Method B).

(5 S,8S)-5-Isobutyl-13-isopropyl-3,6,11,14-tetraoxo-8-(((S)-2-oxopyrrolidin-3-yl) methyl)-1-phenyl-2,10,15-trioxa-4,7,12-triazahexadecane-9-sulfonate (20): Yield (73%), mp 85-87° C. $^1$H NMR (400 MHz, DMSO-$d_6$) δ ppm 8.48 (d, J=7.52 Hz, 1H), 7.61-7.67 (m, 1H), 7.46-7.53 (m, 1H), 7.27-7.42 (m, 5H), 6.38-6.43 (m, 1H), 4.95-5.08 (m, 2H), 4.15-4.24 (m, 1H), 4.03-4.12 (m, 1H), 3.90-4.01 (m, 1H), 3.67 (s, 3H), 3.11 (dd, J=6.35, 13.28 Hz, 2H), 2.31-2.35 (m, 1H), 2.07-2.15 (m, 3H), 1.96-2.05 (m, 2H), 1.91 (dd, J=8.70, 14.20 Hz, 3H), 1.39-1.71 (m, 6H), 1.10 (dt, J=4.49, 7.08 Hz, 1H), 0.76-0.92 (m, 6H). HRMS (ESI) calcd for $C_{28}H_{41}N_4O_{11}S$: [M−]: 641.2498. Found: 641.2464. HPLC purity 98.5% (Method B).

(5 S, 8S)-1-(3-Chlorophenyl)-5-(cyclohexylmethyl)-13-methyl-3,6,11,14-tetraoxo-8-(((S)-2-oxopyrrolidin-3-yl) methyl)-2,10,15-trioxa-4,7,12-triazahexadecane-9-sulfonate (21): Yield (66%), mp 64-66° C. $^1$H NMR (400 MHz, DMSO-$d_6$) δ ppm 8.50 (d, J=7.81 Hz, 1H), 7.61-7.69 (m, 1H), 7.48-7.57 (m, 1H), 7.34-7.44 (m, 2H), 7.30 (d, J=2.93 Hz, 1H), 6.42 (d, J=7.42 Hz, 1H), 5.69-5.77 (m, 1H), 4.94-5.12 (m, 2H), 4.19-4.29 (m, 1H), 4.06-4.17 (m, 1H), 3.81-4.00 (m, 1H), 3.63 (s, 3H), 2.96-3.20 (m, 2H), 2.01-2.29 (m, 2H), 1.82-1.96 (m, 1H), 1.62 (d, J=8.59 Hz, 6H), 1.38-1.52 (m, 4H), 1.23 (d, J=7.23 Hz, 3H), 1.06-1.14 (m, 4H), 0.76-0.94 (m, 2H). HRMS (ESI) calcd for $C_{29}H_{40}ClN_4O_{11}S$: [M−]: 687.2108. Found: 687.2131. HPLC purity 97.4% (Method B).

(5 S,8S)-1-(3-Chlorophenyl)-5-(cyclohexylmethyl)-13-isopropyl-3,6,11,14-tetraoxo-8-(((S)-2-oxopyrrolidin-3-yl) methyl)-2,10,15-trioxa-4,7,12-triazahexadecane-9-sulfonate (22): Yield (62%), mp 82-84° C. $^1$H NMR (400 MHz, DMSO-$d_6$) δ ppm 8.45 (d, J=7.72 Hz, 1H), 7.63-7.71 (m, 1H), 7.48-7.55 (m, 1H), 7.31-7.42 (m, 2H), 7.20 (d, J=3.56 Hz, 1H), 6.47 (d, J=7.61 Hz, 1H), 5.62-5.74 (m, 1H), 4.94-5.12 (s, 2H), 4.19-4.31 (m, 1H), 4.06-4.17 (m, 1H), 3.81-4.02 (m, 1H), 3.63 (s, 3H), 2.96-3.17 (m, 2H), 2.01-2.29 (m, 2H), 1.82-1.96 (m, 1H), 1.62 (m, 6H), 1.38-1.52 (m, 4H), 1.10 (dt, J=4.49, 7.08 Hz, 1H), 1.06-1.14 (m, 4H), 0.97-1.04 (d, J=7.48 Hz, 6H), 0.76-0.94 (m, 2H). HRMS (ESI) calcd for $C_{31}H_{44}ClN_4O_{11}S$: [M−]: 715.2421. Found: 715.2413. HPLC purity 98.3% (Method B).

(5 S,8S)-5-(Cyclohexylmethyl)-13-methyl-3,6,11,14-tetraoxo-8-(((S)-2-oxopyrrolidin-3-yl)methyl)-1-phenyl-2,10,15-trioxa-4,7,12-triazahexadecane-9-sulfonate (23): Yield (72%), mp 61-63° C. $^1$H NMR (400 MHz, DMSO-$d_6$) δ ppm 8.47 (s, 1H), 7.63 (s, 1H), 7.42-7.54 (m, 1H), 7.37 (s, 1H), 7.28-7.40 (m, 5H), 6.52 (t, J=5.91 Hz, 1H), 4.98-5.04 (m, 2H), 4.15-4.28 (m, 1H), 3.87-4.03 (m, 1H), 3.77 (s, 3H), 3.74 (d, J=7.13 Hz, 1H), 3.11 (dd, J=8.84, 19.67 Hz, 2H), 2.02-2.22 (m, 2H), 1.53-1.70 (m, 4H), 1.34-1.52 (m, 4H), 1.05-1.13 (d, J=7.24 Hz, 3H), 0.87-0.98 (m, 6H), 0.76-0.84 (m, 2H). HRMS (ESI) calcd for $C_{29}H_{41}N_4O_{11}S$: [M−]: 653.2498. Found: 653.2483. HPLC purity 97.7% (Method B).

Enzyme Assays and Inhibition Studies.

FRET protease assays. The FRET protease assay (3CL protease) was performed by preparing stock solutions of the substrate (Edans-DFHLQ/GP-Dabcyl, SEQ ID NO:1) and inhibitor in DMSO and diluting into assay buffer which was comprised of 20 mM HEPES buffer, pH 8, containing NaCl (200 mM), 0.4 mM EDTA, glycerol (60%), and 6 mM dithiothreitol (DTT). The protease was mixed with serial dilutions of each compound up to 100 μM or with DMSO in 25 μL of assay buffer and incubated at 37° C. for 30 min, followed by the addition of 25 μL of assay buffer containing substrate. Fluorescence readings were obtained using an excitation wavelength of 360 nm and an emission wavelength of 460 nm on a fluorescence microplate reader (FLx800; Biotec, Winoosk, Vt.) 1 h following the addition of substrate. Relative fluorescence units (RFU) were determined by subtracting background values (substrate-containing well without protease) from the raw fluorescence values. The dose-dependent FRET inhibition curves were fitted with a variable slope by using GraphPad Prism software (GraphPad, La Jolla, Calif.) in order to determine the $IC_{50}$ values of the inhibitors.

Evaluation of the Compounds in Cell-Based Assays.

The effects of each inhibitor on virus replication were examined against NV in the NV replicon harboring cells (HG23 cells). Briefly, confluent and semi-confluent HG23 cells were incubated with medium containing DMSO (<0.1%) or each compound (up to 200 uM) for 48 h. After the incubation, total RNA was extracted and viral genome was quantitated with real-time quantitative RT-PCR (qRT-PCR). The EC50 values were determined by GraphPad-Prism software.

Bioavailability Studies in Rats.

Figure 4:
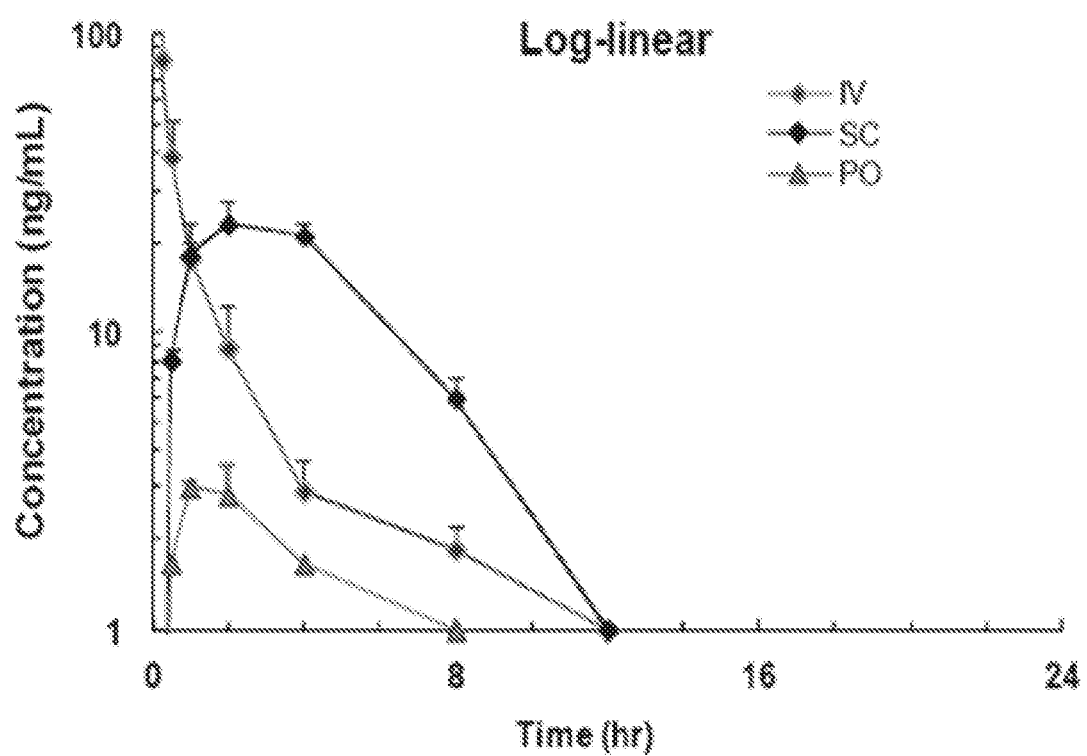

Following the intravenous (IV) subcutaneous (SC) or oral (PO) administration of compound 11 at 1 mg/Kg (body weight) in rats, blood samples were obtained at 0.5, 1, 4, 8, 12, 16 and 24 h. Bioavailability data for the compounds is presented in Table 3 and FIG. 4.

Results and Discussion

The mechanism of action of prodrug (I) is outlined in FIG. 1A where chemical and/or enzymatic hydrolysis of prodrug (I) yields the bisulfite adduct which then reverts to the precursor aldehyde. Subsequent reaction with the catalytic cysteine (Cys139) of norovirus 3CL protease leads to inactivation of the enzyme via the formation of a tetrahedral adduct. The increased lipophilicity of ester prodrug (I) should result in enhanced absorption, followed by chemical and/or enzymatic hydrolysis to yield the bisulfite adduct, which then reverts to the aldehyde (or other warhead), leading to inactivation of the target protease. The rate and extent of absorption of (I) can be modulated by varying the hydrophobic component (R). Carbamate prodrugs (II), though having higher chemical stability than esters, should behave similarly.

The inhibitory activity of the synthesized compounds against NV 3CLpro and their anti-norovirus activity in a cell-based replicon system were evaluated as described. The determined IC50 values in enzyme assay and EC50 values against NV in replicon harboring cells (HG23 cells) are listed in Tables 1 and 2 and they are the average of at least two determinations. The results listed in Table 1 clearly demonstrate that prodrugs 1-17 display significant anti-norovirus activity in replicon cells. Furthermore, these compounds were found to exhibit comparable inhibitory activity against norovirus 3CLpro, as well as norovirus in replicon cells, as the precursor bisulfite adducts and corresponding aldehydes. The m-Cl phenyl substituted derivatives with a cyclohexylalanine (Cha) as the P251 residue (compounds 9-14, Table 1), displayed higher potency because the Cha side chain optimally fills the hydrophobic S2 subsite and the chlorine substituent engages in additional binding interactions. The prime subsites (Sn') of norovirus 3CL protease are shallow, consequently, the prodrug forms 1-17 may be devoid of intrinsic inhibitory activity toward 3CL protease or norovirus, however, under the conditions used to assay the enzyme in vitro or in conducting the replicon harboring cells studies, hydrolysis of the esters yields the corresponding TS inhibitor bisulfite adducts which then revert to the corresponding aldehydes—the actual inhibitory species. This has been confirmed by structural studies where incubation of a peptidyl aldehyde bisulfite adduct with norovirus 3CL protease in 20 mM Tris buffer, pH 8.0, resulted in reversal of the bisulfite adduct to the precursor aldehyde, followed by reaction with the active site cysteine (Cys139), ultimately leading to the formation of an enzyme-aldehyde inhibitor adduct. The high resolution structure of the enzyme-inhibitor complex provides additional confirmation of the mechanism, along with mass spectrometric analysis of the assay results establishing the formation of the aldehyde.

A small number of carbamate prodrugs 18-23 (Table 2) were also synthesized and shown to exhibit potent anti-norovirus activity (Table 2, compounds 18-23). The availability of a large number of natural and unnatural amino acids makes possible the fine tuning of the rate and extent of absorption, as well as release in blood plasma, of the inhibitory species. Likewise, the high potency and lower chemical reactivity of carbonate esters can also be exploited (for example, compound 17 in Table 1).

Bioavailability Studies in Rats.

Following the intravenous (IV), subcutaneous (SC) or oral (PO) administration of compound 11 in rats, most of compound 11 was converted to the aldehyde form (compound 25) in rat plasma when administered via IV, SC and PO routes. Bioavailability was significantly increased by SC administration compared to IV administration (178% from 100%) (Table 3 and FIG. 4), suggests the improvement of bioavailability by the prodrug.

TABLE 3

Summary of PK parameters for compound 25 in rats following a single IV, SC and PO dose of compound 11 at 1 mg/Kg.

| Route | Cmax (ng/mL) | Tmax (h) | AUC (0-24) (ng/mL * h) | AUC (0-inf) (ng/mL * h) | T-half (h) | Bioavailability (%) |
|---|---|---|---|---|---|---|
| PO | 3.2 ± 0.27 | 1.0-2.0 | 10.3 ± 3.8 | 13.8 ± 5.9 | 2.4 ± 1.6 | 17 |
| SC | 24.2 ± 2.6 | 2.0-4.0 | 141 ± 77.7 | 144 ± 77.8 | 2.0 ± 0.39 | 178 |
| IV | 82.2 ± 21.9 | | 77 ± 24.3 | 81 ± 24.7 | 2.5 ± 0.43 | 100 |

It should be noted that the prodrug approach expounded herein can be extended to other TS inhibitors, such as α-ketoamides. Furthermore, previously reported peptidyl or nonpeptidyl TS inhibitors of mammalian, viral, and parasitic serine and cysteine proteases such as, for example, cathepsins L and S, calpains, and falcipain-2, can all be transformed to the corresponding ester and carbamate prodrugs, as described in more detail in Example 4.

In conclusion, a general approach toward the optimization of the pharmacokinetics of peptidyl or non-peptidyl transition state inhibitors and mimics is disclosed. The approach has wide applicability and provides an effective means of augmenting the therapeutic potential of these classes of inhibitors.

Example 2

The importance of the approach described above can be further extended to peptidyl or non-peptidyl transition state mimics such as, for example, α-hydroxyphosphonates. Prodrug III compounds were synthesized by refluxing a representative peptidyl α-hydroxyphosphonate with an array of anhydrides to yield the corresponding esters (Table 4) which were subsequently shown to inhibit the viral protease in vitro and to display anti-norovirus activity in cell replicon cells.

TABLE 4

Ester prodrug of peptidyl α-hydroxyphosphonate.

(III)

| Compound | $R_3$ | $R_4$ | R | $EC_{50}$ (μM) |
|---|---|---|---|---|
| 27 | H | Isobutyl | $CH_3$ | >1 |
| 28 | | | $(CH_2)_2CH_3$ | 2.8 |
| 29 | | | $(CH_2)_4CH_3$ | 3.8 |
| 30 | | | $(CH_2)_{14}CH_3$ | 4.1 |
| 31 | m-Cl | Cha | $CH_3$ | 0.6 |
| 32 | | | $(CH_2)_6CH_3$ | 0.7 |
| 33 | | | $(CH_2)_{14}CH_3$ | 1.1 |

Example 3

In order to further broaden the scope of our studies, a representative aldehyde bisulfite adduct was covalently attached to polyethylene glycol (PEG) to improve its pharmacokinetic and pharmacodynamic characteristics. PEGylation of the aldehyde bisulfite adduct was accomplished by reacting the compound with succinic anhydride. The resulting hemisuccinate bisulfite adduct was added to mPEG5000-OH, followed by EDCI and HOBt in a minimum amount of dry dichloromethane. Triethylamine was added to pH 8 and the mixture was stirred for 18 h at room temperature. Addition of diethyl ether yielded a precipitate which was collected and purified by recrystallization. The PEGylated inhibitor was then screened against norovirus 3CL protease and against norovirus in replicon cells.

PEGylated compound 25 was generated and its activity in protease assay and cell-based assay demonstrated $IC_{50}$ and $EC_{50}$ were 0.1 and 0.03 μM, respectively, which is comparable to the aldehyde counterpart, compound 25.

Example 4

Lastly, previously reported peptidyl or nonpeptidyl TS inhibitors of mammalian, viral, and parasitic serine and cysteine proteases such as, for example, cathepsins L and S, calpains, and falcipain-2, can all be transformed to the corresponding ester and carbamate prodrugs. To demonstrate this, we used known cathepsin L, falcipain-2, and calpain inhibitors and synthesized prodrug forms using the approach outlined in Example 1.

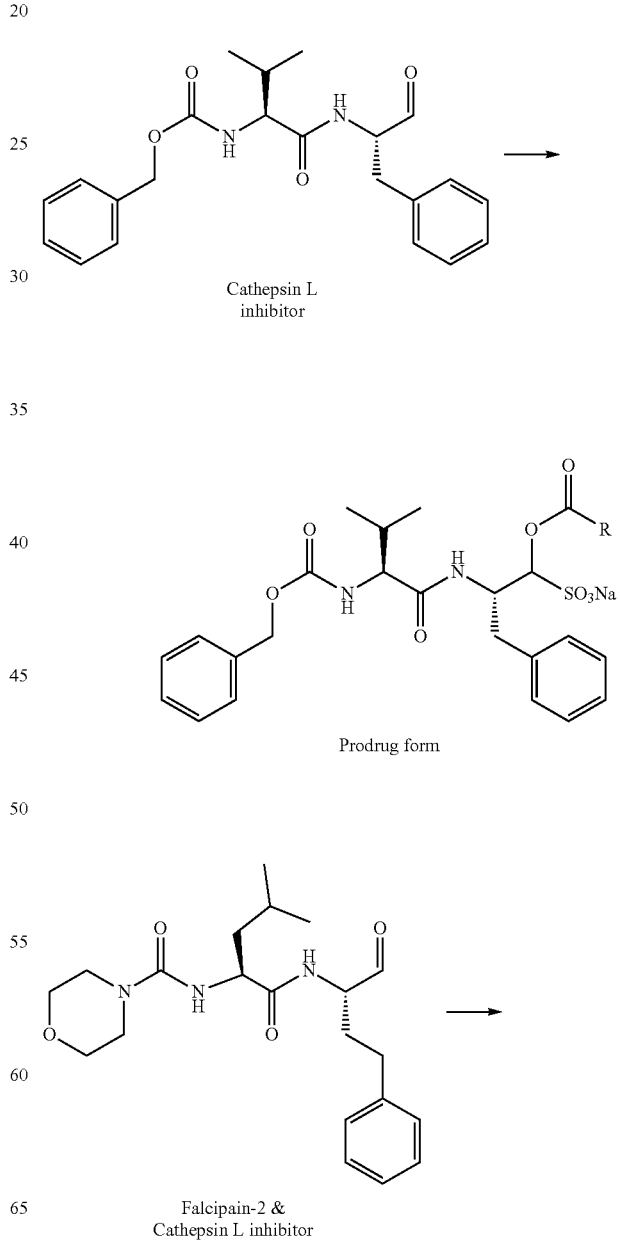

23
-continued

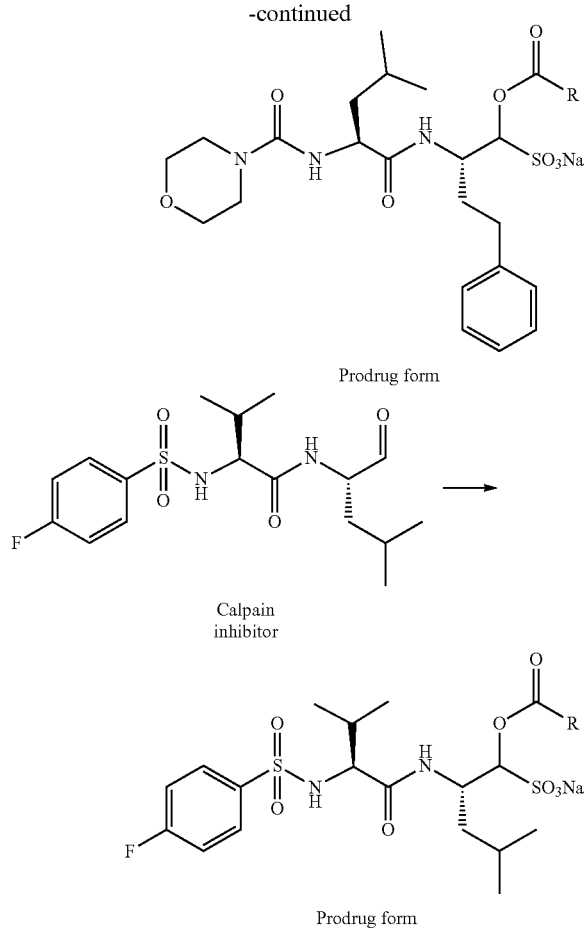

The prodrugs (R=CH₃ and —(CH₂)₆CH₃) of the cathepsin L inhibitor were generated and enzyme inhibition (cathepsin L inhibition) assay with the prodrugs demonstrated that their IC$_{50s}$ were approximately 0.003 µM. This IC$_{50}$ was comparable to that of cathepsin L inhibitor (aldehyde), suggesting the prodrugs retained their activity and should improve the bioavailability in animals and humans. The prodrugs were shown to be highly effective inhibitors of the target enzymes—comparable to aldehyde counterparts. Thus, the approach described herein can, in principle, be extended to any peptidyl or non-peptidyl transition state inhibitor of serine and cysteine proteases.

24

The invention claimed is:
1. A compound having a structure selected from the group consisting of:

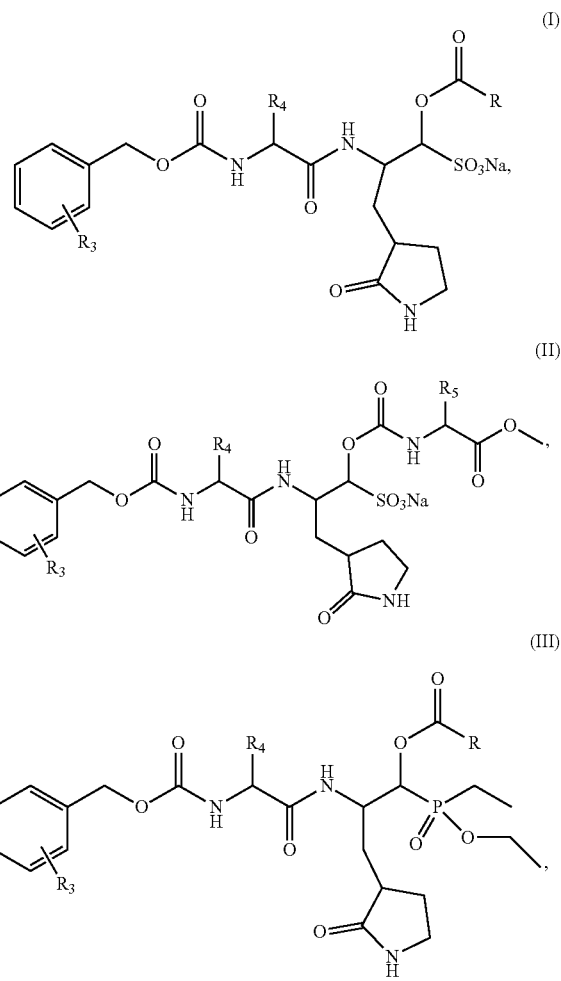

and pharmaceutically acceptable salts thereof,
wherein:
each R is selected from the group consisting of —H, branched or unbranched alkyls, substituted or unsubstituted aryls, substituted or unsubstituted arylalkyls, alkoxys, —CHR₇NHR₈, and —(CH₂)$_m$W, where R₇ is H or a side chain of a natural or unnatural amino acids,

SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic FRET substrate

<400> SEQUENCE: 1

Asp Phe His Leu Gln Gly Pro
1               5 and R$_8$ is —H, a branched or unbranched alkyl, or carboxylalkyl, and where W is —COOR$_6$, —NH$_2$, —NHR$_6$, —NH(C=O)R$_6$, —(C=O)NH$_2$, or —(C=O)NHR$_6$, and m is 1-10, and each R$_6$ is —H, a branched or unbranched alkyl, a substituted or unsubstituted phenyl, a substituted or unsubstituted aryl or a substituted or unsubstituted arylalkyl;

each R$_3$ is selected from the group consisting of —H, o-F, m-F, p-F, o-Cl, m-Cl, p-Cl, o-Br, m-Br, p-Br, fluoroalkyl, —CN, —OR$_9$, —COOR$_{10}$, and —(C=O)NR$_{10}$R$_{10}$, where R$_9$ is a branched or unbranched alkyl or fluoroalkyl, and where each R$_{10}$ is H or a branched or unbranched alkyl;

each R$_4$ is a side chain of a natural or unnatural amino acid; and each R$_5$ is selected from the group consisting of —H, and a side chain of a natural or unnatural amino acid.

2. The compound of claim 1, further comprising polyethylene glycol covalently attached to said compound.

3. A compound having a structure selected from the group consisting of:

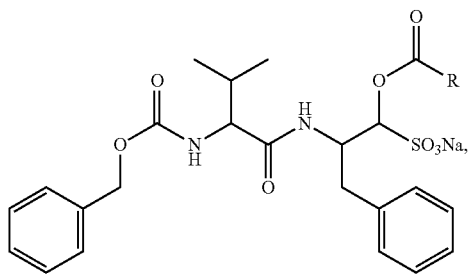

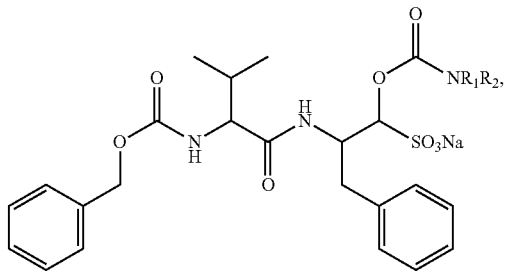

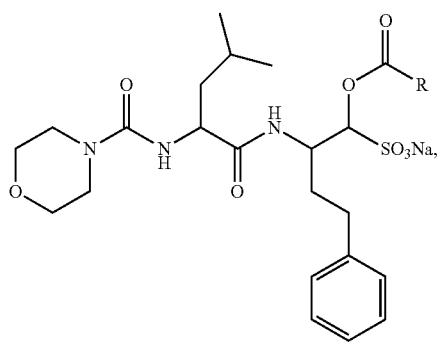

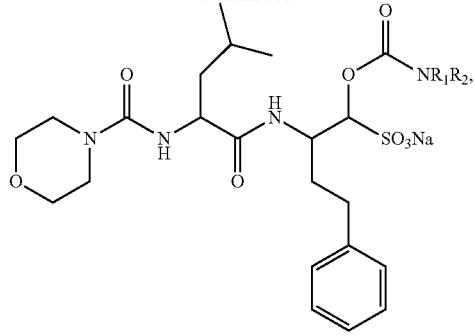

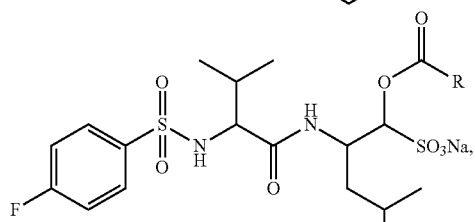

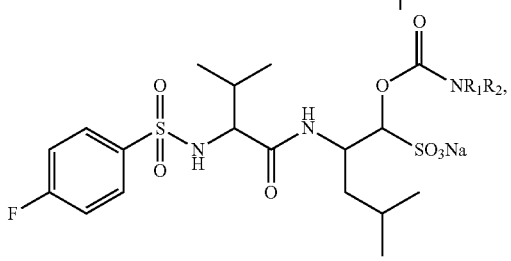

and pharmaceutically acceptable salts thereof, wherein:
each R is selected from the group consisting of —H, branched or unbranched alkyls, substituted or unsubstituted aryls, substituted or unsubstituted arylalkyls, alkoxys, —CHR$_7$NHR$_8$, and —(CH$_2$)$_m$W, where R$_7$ is H or a side chain of a natural or unnatural amino acids, and R$_8$ is —H, a branched or unbranched alkyl, or carboxyalkyl, and where W is —COOR$_6$, —NH$_2$, —NHR$_6$, —NH(C=O)R$_6$, —(C=O)NH$_2$, or —(C=O)NHR$_6$, m is 1-10, and each —R$_6$ is —H, a branched or unbranched alkyl, a substituted or unsubstituted phenyl, a substituted or unsubstituted aryl, or a substituted or unsubstituted arylalkyl;

each R$_1$ is selected from the group consisting of —H, branched or unbranched alkyls, substituted or unsubstituted phenyls, substituted or unsubstituted aryls, substituted or unsubstituted arylalkyls, and halogenated alkyls; and each R$_2$ is selected from the group consisting of —H, branched or unbranched alkyls, substituted or unsubstituted phenyls, substituted or unsubstituted aryls, substituted or unsubstituted arylalkyls, halogenated alkyls, and —CHR$_7$COOR$_8$, where R$_7$ is H or a side chain of a natural or unnatural amino acid, and R$_8$ is H or a branched or unbranched alkyl.

4. A method of inhibiting serine or cysteine protease activity in a subject, said method comprising administering to said subject a therapeutically-effective amount of a first compound according to claim 1.

5. The method of claim 4, wherein said first compound is metabolized in said subject to yield an active metabolite that inhibits serine or protease activity in said subject.

6. The method of claim 4, further comprising administering a second compound to said subject.

7. The method of claim 6, wherein said second compound is a compound according to claim 1, said first compound being different from said second compound.

8. The method of claim 6, wherein said first and second compounds are co-administered.

9. The method of claim 4, wherein said first compound inhibits 3C or 3C-like protease activity of one or more viruses selected from the group consisting of caliciviruses, picornaviruses, and coronaviruses.

10. The method of claim 4, wherein the subject suffers from a condition selected from the group consisting of malaria, tumor cell growth, stroke, heart attack, neural degeneration, cataracts, and glaucoma.

11. A composition comprising a first compound according to claim 1 dispersed in a pharmaceutically-acceptable carrier.

12. The composition of claim 11, further comprising a second compound, both of said compounds being dispersed in said pharmaceutically-acceptable carrier.

13. The composition of claim 12, wherein said second compound is a compound according to claim 1, said first compound being different from said second compound.

14. A kit comprising: a first compound according to claim 1; and instructions for administering said first compound to a subject in need thereof.

15. The kit of claim 14, wherein said first compound is provided in unit dosage form.

16. The kit of claim 14, wherein said first compound is provided in a first container, said kit further comprising a carrier in a second container; and instructions for preparing said first compound for administration to said subject.

17. A method of preventing or inhibiting replication of a virus in a cell, said method comprising contacting said cell with a first compound according to claim 1, wherein said virus is selected from the group consisting of caliciviruses, picornaviruses, coronaviruses, and combinations thereof.

18. The method of claim 17, wherein said virus is selected from the group consisting of Norwalk virus, feline calicivirus, MD145, middle east respiratory syndrome coronavirus, murine norovirus, vesicular exanthema of swine virus, rabbit hemorrhagic disease virus, enterovirus 71, poliovirus, coxsackievirus, foot-and-mouth disease virus, hepatitis A, porcine teschovirus, rhinovirus, human coronavirus, transmissible gastroenteritis virus, murine hepatitis virus, bovine coronavirus, feline infectious peritonitis virus, and severe acute respiratory syndrome coronavirus.

19. The compound of claim 1, having a structure selected from the group consisting of Compound 1, 2, 3, 4, 5, 6, 7, 8, 9, 10, 11, 12, 13, 14, 15, 16, 17, 18, 19, 20, 21, 22, 23, 27, 28, 29, 30, 31, 32, 33, and pharmaceutically acceptable salts thereof.

* * * * *